United States Patent
Chahine

(10) Patent No.: US 11,963,737 B2
(45) Date of Patent: Apr. 23, 2024

(54) METHOD FOR SENSING AND COMMUNICATION OF BIOMETRIC DATA AND FOR BIDIRECTIONAL COMMUNICATION WITH A TEXTILE BASED SENSOR PLATFORM

(71) Applicant: MYANT INC., Toronto (CA)

(72) Inventor: Tony Chahine, Toronto (CA)

(*) Notice: Subject to any disclaimer, the term of this patent is extended or adjusted under 35 U.S.C. 154(b) by 0 days.

(21) Appl. No.: 16/950,334

(22) PCT Filed: May 22, 2019

(86) PCT No.: PCT/CA2019/050697
§ 371 (c)(1),
(2) Date: Nov. 17, 2020

(87) PCT Pub. No.: WO2019/222846
PCT Pub. Date: Nov. 28, 2019

(65) Prior Publication Data
US 2021/0315458 A1    Oct. 14, 2021

Related U.S. Application Data

(60) Provisional application No. 62/674,683, filed on May 22, 2018.

(51) Int. Cl.
*G08B 1/08* (2006.01)
*A41D 1/00* (2018.01)
(Continued)

(52) U.S. Cl.
CPC ............ *A61B 5/0024* (2013.01); *A41D 1/002* (2013.01); *A61B 5/015* (2013.01); *A61B 5/6823* (2013.01);
(Continued)

(58) Field of Classification Search
CPC ..... A61B 5/0024; A61B 5/015; A61B 5/6823; A61B 5/6828; A61B 5/7455; H04W 4/38; A41D 1/002; D02G 3/441
See application file for complete search history.

(56) References Cited

U.S. PATENT DOCUMENTS 6,095,996 A * 8/2000 Steer ................. A61L 15/585
                                               428/355 R
9,721,409 B2 * 8/2017 Sezan ................. G16H 10/65
(Continued)

FOREIGN PATENT DOCUMENTS

CN   103536278 A    1/2014
CN   104768455 A    7/2015
(Continued)

OTHER PUBLICATIONS

Anne Trafton, Sensors woven into a shirt can monitor vital signs (Year: 2020).*
(Continued)

*Primary Examiner* — Quang Pham
(74) *Attorney, Agent, or Firm* — NORTON ROSE FULBRIGHT CANADA LLP

(57) ABSTRACT

A method of using bidirectionally a sensor platform incorporated into a garment of a wearer using a plurality of sensed biometric data, the method comprising: receiving from sensors of the sensor platform a set of the plurality of biometric data; sending the set to network device associated with the sensor platform; receiving a response including a command from the network device; and applying the command via one or more actuators of the sensor platform to effect a change in an operational characteristic of at least one of the sensors of the sensor platform.

10 Claims, 13 Drawing Sheets

(51) Int. Cl.
    *A61B 5/00*     (2006.01)
    *A61B 5/01*     (2006.01)
    *D02G 3/44*     (2006.01)
    *H04W 4/38*     (2018.01)

(52) U.S. Cl.
    CPC .......... *A61B 5/6828* (2013.01); *A61B 5/7455* (2013.01); *D02G 3/441* (2013.01); *H04W 4/38* (2018.02)

(56) References Cited

U.S. PATENT DOCUMENTS

| | | | |
|---|---|---|---|
| 10,037,672 B1* | 7/2018 | Abraham | A61B 5/02055 |
| 10,258,259 B1* | 4/2019 | Zets | A61B 5/7455 |
| 2007/0063849 A1* | 3/2007 | Rosella | A41D 1/002 340/573.1 |
| 2009/0287191 A1* | 11/2009 | Ferren | A61B 8/06 600/504 |
| 2010/0141407 A1* | 6/2010 | Heubel | G06F 1/163 340/407.1 |
| 2011/0118653 A1* | 5/2011 | Eckhoff | A61B 5/441 604/20 |
| 2011/0118695 A1* | 5/2011 | Eckhoff | A61K 31/195 604/501 |
| 2011/0118698 A1* | 5/2011 | Eckhoff | A61B 5/1116 604/503 |
| 2013/0144379 A1* | 6/2013 | Najafi | A61B 5/02055 623/2.11 |
| 2014/0006046 A1* | 1/2014 | Feldman | G06Q 10/10 705/2 |
| 2014/0070957 A1 | 3/2014 | Longinotti-buitoni | |
| 2014/0222943 A1* | 8/2014 | Oleson | A61B 5/7214 709/208 |
| 2014/0358193 A1* | 12/2014 | Lyons | A61N 1/37229 607/48 |
| 2014/0375470 A1* | 12/2014 | Malveaux | A61B 5/7275 340/870.01 |
| 2015/0022362 A1* | 1/2015 | Lucas | A61B 5/6828 340/573.7 |
| 2015/0107034 A1* | 4/2015 | Shani | A46B 15/0006 15/22.1 |
| 2015/0152852 A1* | 6/2015 | Li | D04C 1/02 60/527 |
| 2015/0157435 A1* | 6/2015 | Chasins | A61D 13/00 600/549 |
| 2015/0182130 A1* | 7/2015 | Utter, II | A61B 5/0024 600/483 |
| 2015/0186609 A1* | 7/2015 | Utter, II | A61B 5/742 600/301 |
| 2015/0208739 A1* | 7/2015 | Taylor | H05B 3/342 219/211 |
| 2015/0230524 A1* | 8/2015 | Stevens | H05B 1/02 219/494 |
| 2015/0250420 A1* | 9/2015 | Longinotti-Buitoni | A61B 5/1135 600/534 |
| 2015/0333572 A1* | 11/2015 | Leabman | H02J 50/402 320/108 |
| 2016/0100798 A1* | 4/2016 | Markel | A42B 1/006 600/509 |
| 2016/0228640 A1 | 8/2016 | Pindado | |
| 2016/0324677 A1* | 11/2016 | Hyde | A61B 5/01 |
| 2017/0010664 A1* | 1/2017 | Tanaka | H04L 63/0869 |
| 2017/0056644 A1* | 3/2017 | Chahine | A61N 1/36014 |
| 2017/0060298 A1* | 3/2017 | Hwang | A61B 5/6807 |
| 2017/0086743 A1* | 3/2017 | Bushnell | A61B 5/681 |
| 2017/0119318 A1* | 5/2017 | Shay | A61B 5/7225 |
| 2017/0156640 A1* | 6/2017 | Robucci | G06F 3/0346 |
| 2017/0216078 A1* | 8/2017 | Rivlin | A61F 5/05866 |
| 2017/0230734 A1* | 8/2017 | Oleson | H04W 4/80 |
| 2017/0231793 A1* | 8/2017 | Parr | A61F 5/0111 601/84 |
| 2017/0249810 A1* | 8/2017 | Zerick | G08B 6/00 |
| 2017/0251933 A1* | 9/2017 | Braun | A61B 5/117 |
| 2017/0258995 A1* | 9/2017 | Hyde | A61M 35/10 |
| 2017/0281074 A1* | 10/2017 | D'Lima | A61B 5/4842 |
| 2017/0319132 A1* | 11/2017 | Longinotti-Buitoni | A61B 5/0002 |
| 2017/0367654 A1* | 12/2017 | Cheng | A61B 5/6833 |
| 2018/0000367 A1* | 1/2018 | Longinotti-Buitoni | A41D 13/1281 |
| 2018/0052516 A1* | 2/2018 | Efrati | G06F 3/018 |
| 2018/0068538 A1* | 3/2018 | Kessler | G08B 6/00 |
| 2018/0087193 A1* | 3/2018 | Fu | D03D 1/0088 |
| 2018/0114081 A1* | 4/2018 | Dejewski | G06V 40/70 |
| 2018/0161002 A1* | 6/2018 | Alford | A61B 8/085 |
| 2018/0220933 A1* | 8/2018 | Jung | A61B 5/6804 |
| 2018/0272147 A1* | 9/2018 | Freeman | G16H 50/30 |
| 2018/0279947 A1* | 10/2018 | Ummat | A61B 5/0022 |
| 2018/0289313 A1* | 10/2018 | Inan | A61B 5/0537 |
| 2018/0304038 A1* | 10/2018 | Jafri | A61M 16/201 |
| 2018/0321700 A1* | 11/2018 | Kwak | G05D 23/1919 |
| 2019/0000384 A1* | 1/2019 | Gupta | A61B 5/6804 |
| 2019/0056707 A1* | 2/2019 | Pollard | A61B 5/165 |
| 2020/0093383 A1* | 3/2020 | Arkans | A61B 5/02141 |
| 2020/0113518 A1* | 4/2020 | Mollohan | G06F 1/163 |
| 2020/0314184 A1* | 10/2020 | Etemad | G16H 40/67 |
| 2020/0367823 A1* | 11/2020 | Chahine | A41B 11/00 |
| 2022/0084672 A1* | 3/2022 | Hall | A61B 5/14551 |

FOREIGN PATENT DOCUMENTS

| | | |
|---|---|---|
| CN | 107427230 A | 12/2017 |
| EP | 2374049 | 10/2011 |
| WO | 2015138515 A1 | 9/2015 |

OTHER PUBLICATIONS

Dunne et al., A Method of Measuring Garment Movement for Wearable Sensing (Year: 2011).*
Ratanen et al., Improving Human Thermal Comfort with Smart Clothing (Year: 2001).*
Sayem et al., Review on Smart Electro-Clothing Systems (SeCSs) (Year: 2020).*
Angelucci et al., Smart Textiles and Sensorized Garments for Physiological Monitoring A Review of Available Solutions and Techniques (Year: 2021).*
Fernandez-Carames et al., Towards the Internet of Smart Clothing a Review on IoT Wearables and Garments for Creating Intelligent Connected E-Textiles (Year: 2018).*
Sayem et al., Review on Smart Electro-Clothing Systems (SeCSs) (Year: 2019).*
Chen et al., Electronic Textiles for Wearable Point-of-Care Systems (Year: 2022).*
Li et al., From Diagnosis to Treatment Recent Advances in Patient-Friendly Biosensors and Implantable Devices (Year: 2021).*
WIPO, International Search Report and Written Opinion for PCT Application No. PCT/CA2019/050697 dated Sep. 4, 2019.
EPO, Partial Search Report for EP Application No. 19807343.9 dated Feb. 2, 2022.
Beach A et al: "Touch Me Wear: Getting Physical with Social Networks", Computational Science and Engineering, 2009. CSE '09. International Conference on, IEEE, Piscataway, NJ, USA, Aug. 29, 2009 (Aug. 29, 2009), pp. 960-965, XP031543694, ISBN: 978-1-4244-5334-4 the whole document.
Luisa Von Radziewsky et al: "Scarfy", Tangible, Embedded, and Embodied Interaction, ACM, 2 Penn Plaza, Suite 701 New York NY 10121-0701 USA, Jan. 15, 2015 (Jan. 15, 2015), pp. 313-316, XP058065265, DOI: 10.1145/2677199.2680568 ISBN: 978-1-4503-3305-4 the whole document.
Gilsoo Cho, "Smart Clothing Technology and Applications", Retrieved from the Internet: URL:http://www.petronet.ir/documents/10180/2323250/Smart_Clothing_-Technology_and_Applications_(Human_Factors_and_Ergonomics)-Gilsoo_Cho [retrieved on Oct. 8, 2014] Jan. 1, 2010 (Jan. 1, 2010), XP055145274, ISBN: 978-1-42-008852-6.

(56) References Cited

OTHER PUBLICATIONS

EPO, Supplementary Search Report for EP Application No. 19807343.9 dated Jun. 8, 2022.

* cited by examiner

Improve your State of Mind

Detect what makes you stressed, and use our app to get you back into the right state of mind. SKIIN's smart notifications can remind you to breathe after a stressful event, and cope with the things life throws at you.

43

Optimize Sleep

If you're constantly tired in the mornings, it's probably related to the efficiency of your sleep. SKIIN uses the most advanced sensors located on the waistband of the garment to accurately track your sleep. Wake up feeling refreshed.

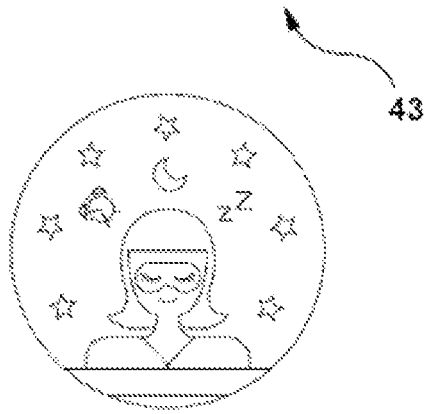

43

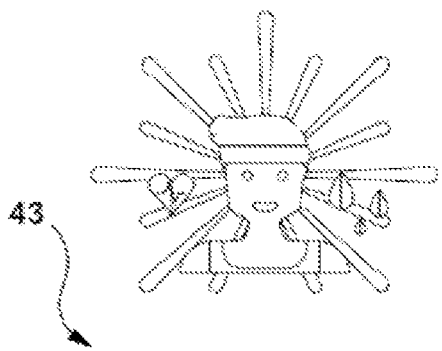

Be Active, Feel Better

Being active is important to your physical and mental health. SKIIN can tell you if you're spending enough time on your feet, taking enough steps, and keeping your posture upright.

43

Control your Home

Your smart home should react to you, not the other way around. Use SKIIN to control your thermostat, lights and speakers based on your mood and body temperature.

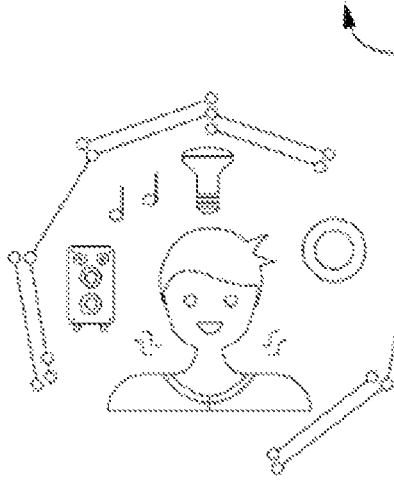

43

FIG. 4

METHOD FOR SENSING AND COMMUNICATION OF BIOMETRIC DATA AND FOR BIDIRECTIONAL COMMUNICATION WITH A TEXTILE BASED SENSOR PLATFORM

CROSS-REFERENCE TO RELATED APPLICATIONS

This application claims the benefits of U.S. Provisional Patent Application Ser. No. 62/674,683, filed on May 22, 2018; the entire contents of which are hereby incorporated by reference herein.

FIELD

The present disclosure relates to bidirectional sensing systems for biometric data.

BACKGROUND

Sensing of biometric data in today's technological based environment is key to understanding and affecting the state of a garment wearer. In particular, athletes and medical patients, among a number of other consumers, are key individuals for much needed accurate and up-to-date (i.e. real-time) biometric sensing, in order to influence (e.g. change) operational characteristics of networked devices in the vicinity of the wearer and/or to communicate on a physical level with the wearer, as expressed by biometric data. However, state of the art sensor arrangements and methods of data processing are cumbersome and have limited applicability and adaptability to a wearer's varied lifestyle, including ever-changing physical and mental states.

SUMMARY

It is an object of the present invention to provide a sensing platform and method of use thereof to obviate or mitigate at least one of the above presented disadvantages.

A first aspect provided is a method of using bidirectionally a sensor platform incorporated into a garment of a wearer using a plurality of sensed biometric data, the method comprising: receiving from sensors of the sensor platform a set of the plurality of biometric data; sending the set to network device associated with the sensor platform; receiving a response including a command from the network device; and applying the command via one or more actuators of the sensor platform to effect a change in an operational characteristic of at least one of the sensors of the sensor platform.

A second aspect provided is a method of using bidirectionally a sensor platform incorporated into a garment of a wearer using a plurality of sensed biometric data, the method comprising: receiving from sensors of the sensor platform a first set of the plurality of biometric data; sending the first set to network device associated with the sensor platform, the network device having an operational characteristic associated with the set such that the operational characteristic is changed based on applying the first set to the networked device; receiving a response including an acknowledgement of the first set from the network device; receiving from sensors of the sensor platform a second set of the plurality of biometric data; and sending the second set to network device, the network device monitoring whether the change in the operational characteristic based on analyzing the second set.

BRIEF DESCRIPTION OF THE DRAWINGS

The foregoing and other aspects will now be described by way of example only with reference to the attached drawings, in which:

FIG. 1b is an alternative embodiment of the sensor platform of FIG. 1a;

FIG. 4 shows example applications of the biometric data combinations;

FIGS. 8 and 9 show further embodiments of the sensors of FIG. 1a;

DETAILED DESCRIPTION

Figure 1A:
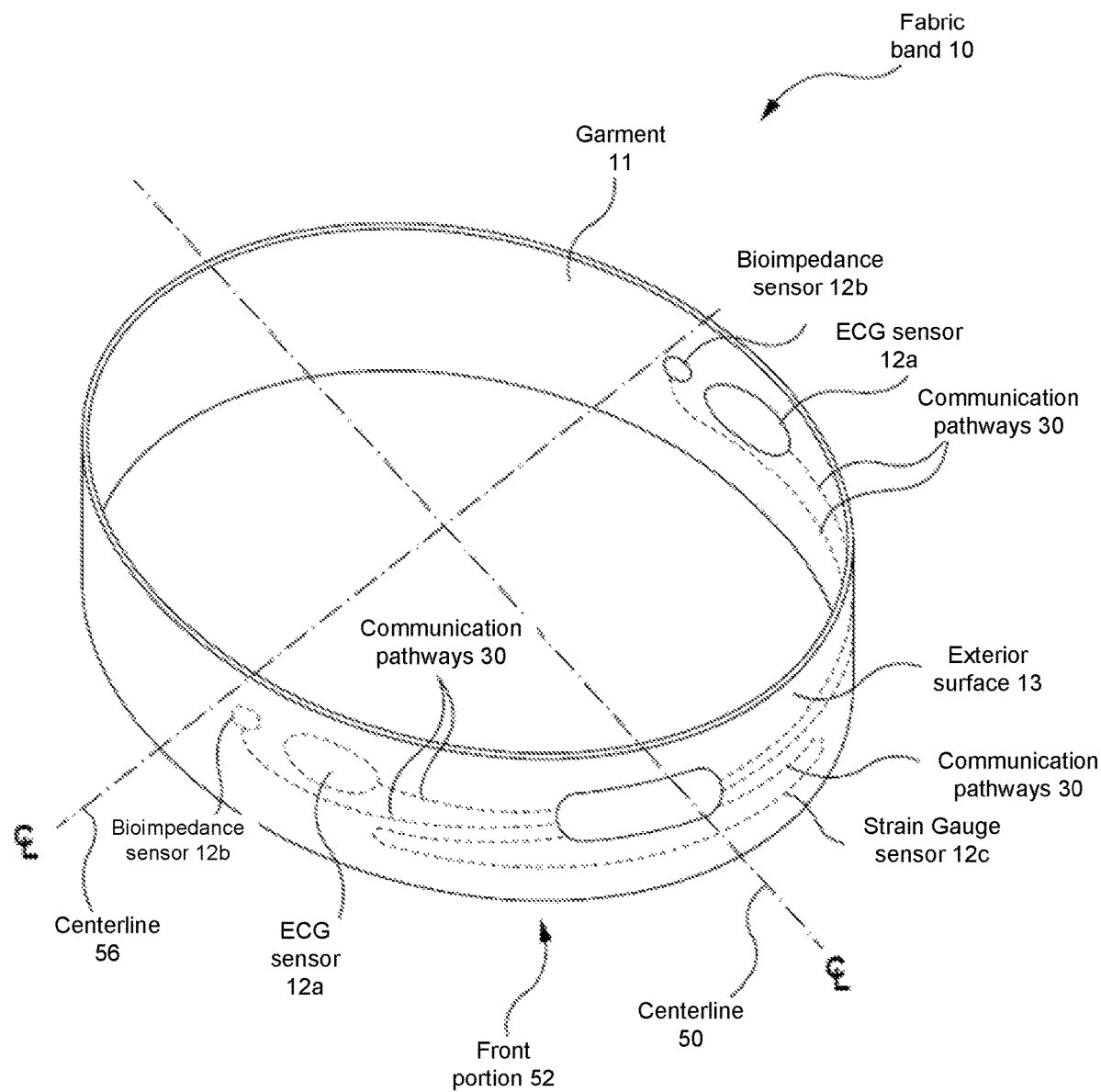
FIG. 1a is a perspective view of a band containing a plurality of sensors.
Figure 1B:
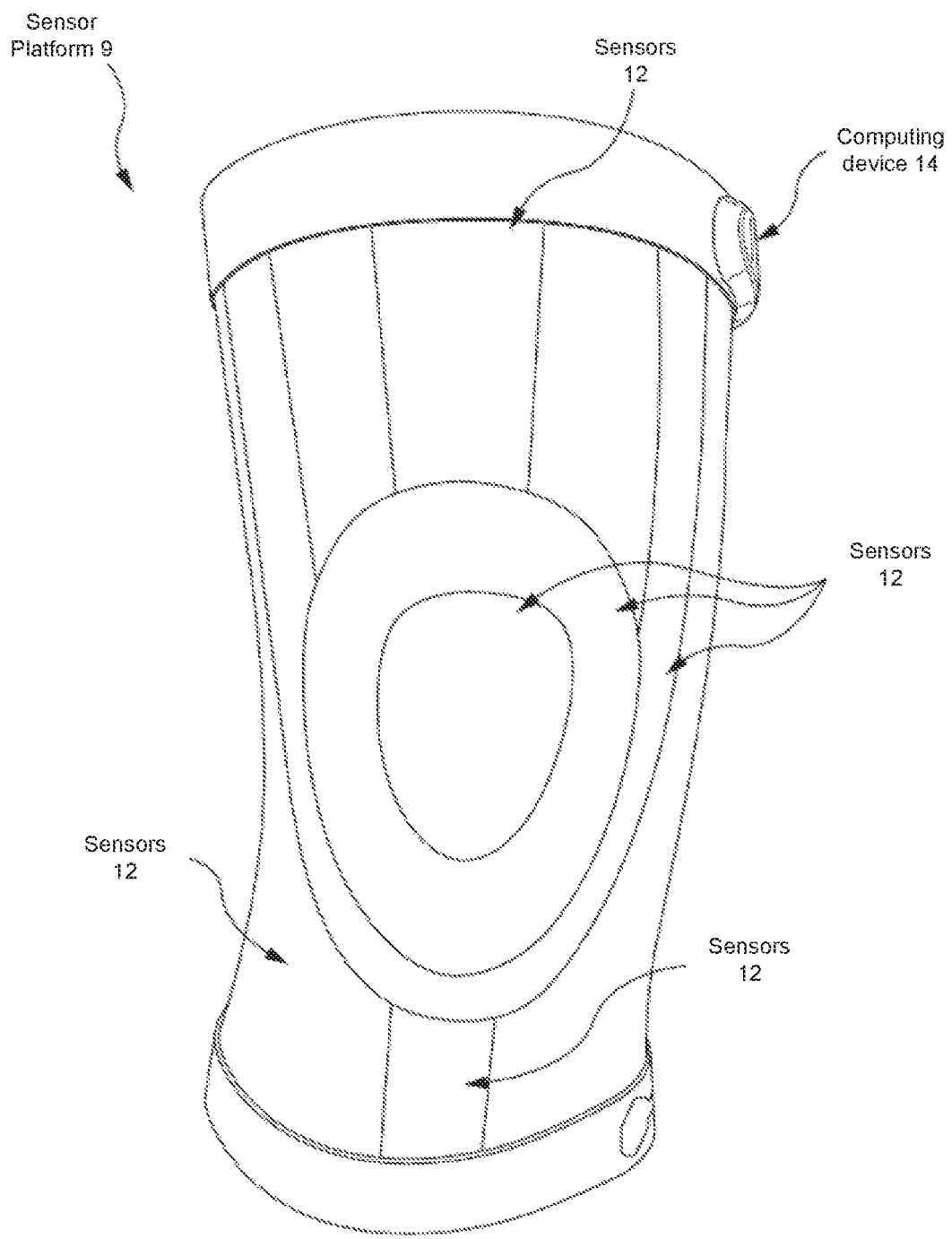
Figure 1C:
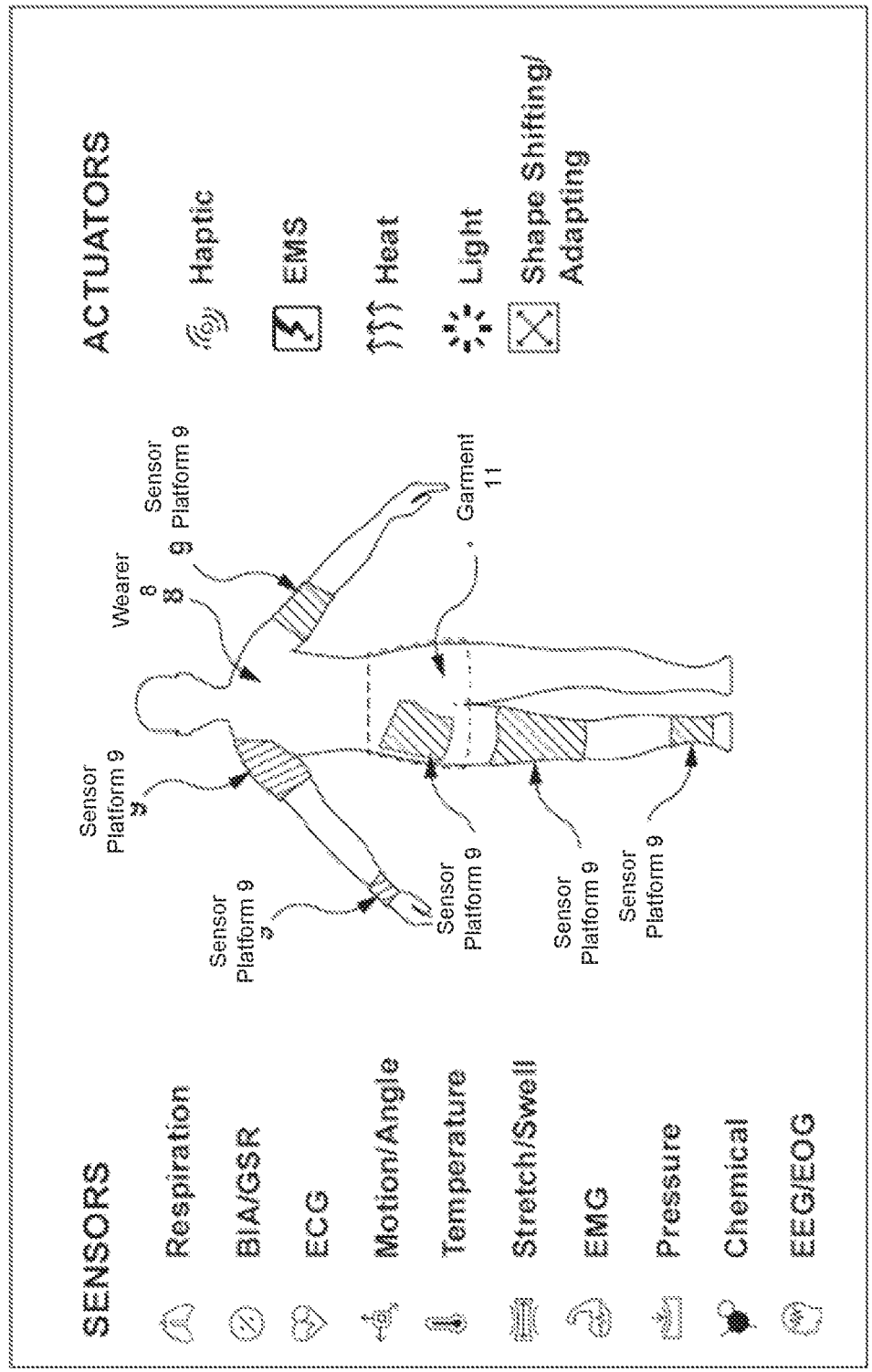
FIG. 1c is an alternative embodiment of the sensor platforms of FIGS. 1a and 1b.

Referring to FIG. 1a, shown is a fabric band 10, as one non-limiting example of a textile based sensor platform 9 integrated into a garment 11, preferable having a resilient knit type, for fitting around a body part of a wearer 8, in order to collect and receive different modes/types of biometric data based on the type/number of sensors 12 (of the sensor platform 9—see FIG. 10) positioned either on or otherwise knit/woven (e.g. embroidered) into the fabric making up the body of the band 10, e.g. the garment 11 itself or otherwise coupled to the garment 11. As such, the sensors 12 (also referred to as actuators 12) can be fabric sensors/actuators 12, such that the sensors/actuators 12 comprise one or more electrically conductive threads woven/knit into a base fabric layer of the garment 11. It is further recognized that the sensor platform 9 can be integrated into the fabric (e.g. textile) of the garment 11 in one or more locations of the garment 11, hence providing for a distributed or a localized sensor platform(s) of the garment 11. For example, the garment 11 can be a sleeve (see FIG. 1b) for fitting over a limb or other extremity (e.g. head, neck, foot, ankle) of the wearer 8, can be a form fitting article of clothing for fitting over the torso of the wearer 8, the midsection (including the buttocks) of the wearer 8 and other body parts of the wearer 8 as would be apparent to a person skilled in the art for practicing the invention(s) as claimed herein—see FIG. 1c.

Also as described below, are biometric data 44a collected (i.e. representative of biosignals generated by the body of the wearer 8 via the sensors 12 of the sensor platform 9) and biometric data 44b expressed, i.e. representative of biosignals received (e.g. from a networked user 6 remote from the wearer 8) over a communications network 22—for example, for subsequent processing by the actuators 12. Alternatively, the biometric data 44b expressed by the sensor platform 9 can be collected by a computing device 14 (see FIG. 3) and processed by the computing device 14 to generate the biometric data 44b for consumption by the sensors/actuators 12 of the sensor platform 9. As such, the sensor platform 9 can be referred to as a bidirectional sensor platform 9, whereby biometric data 44a is collected via the sensors 12 of the sensor platform 9, while the actuators 12 are used to express the biometric data 44b in response to the collected biometric data 44a. For example, the biometric data 44b can be received by (or otherwise generated by) the computing device 14 as one or more commands 45 for sending to the sensors/actuators 12 (for subsequent processing thereby) of the sensor platform 9 of the wearer 8.

As further described below, one example of the bidirectional nature of the sensor platform 9 is where temperature sensors 12 provide the biometric data 44a (e.g. output signals of the sensor platform 9) and heating elements as heating actuators 12 process the received biometric data 44b (e.g. as inputs to the sensor platform 9). For example, a garment 11 that can generate heat for wearers 8 that feel cold or need a skin contact based heating unit (e.g. actuator 12). The textile integrated temperature sensor 12 can monitor the wearer's 8 temperature and feedback that as biometric data 44a to the computing device 14 (see FIG. 3), which can regulate the introduction of heat to the garment 11 via the heat actuators 12, similar to a thermostat. In this case, operation of the sensor platform 9 can be customized and tuned to the personal requirements of each wearer 8, providing temperature profiles that are personalized and work per qualitative sensory requirements. It is recognized that the computing device 14 can control the operation of the sensor platform 9 as a stand-alone unit. Alternatively, the computing device 14 can be in communication (via the communications network 22) with one or more networked devices 40, 60 (see FIGS. 3, 10), each running their respective applications 100,102 for interpreting the biometric data 44a (e.g. received from the computing device 14 as sourced from the sensor platform 9) and for providing (e.g. to the computing device 14 for subsequent operation of the sensors/actuators 12 using the biometric data 44b) the biometric data 44b for expression by the sensor platform 9 in response. In any case, it should be recognized that the sensor platform 9 containing the sensors/actuators 12) operates as a textile based sensor platform in a bidirectional manner, i.e. generates the biometric data 44a and consumes the biometric data 44b.

Figure 13:
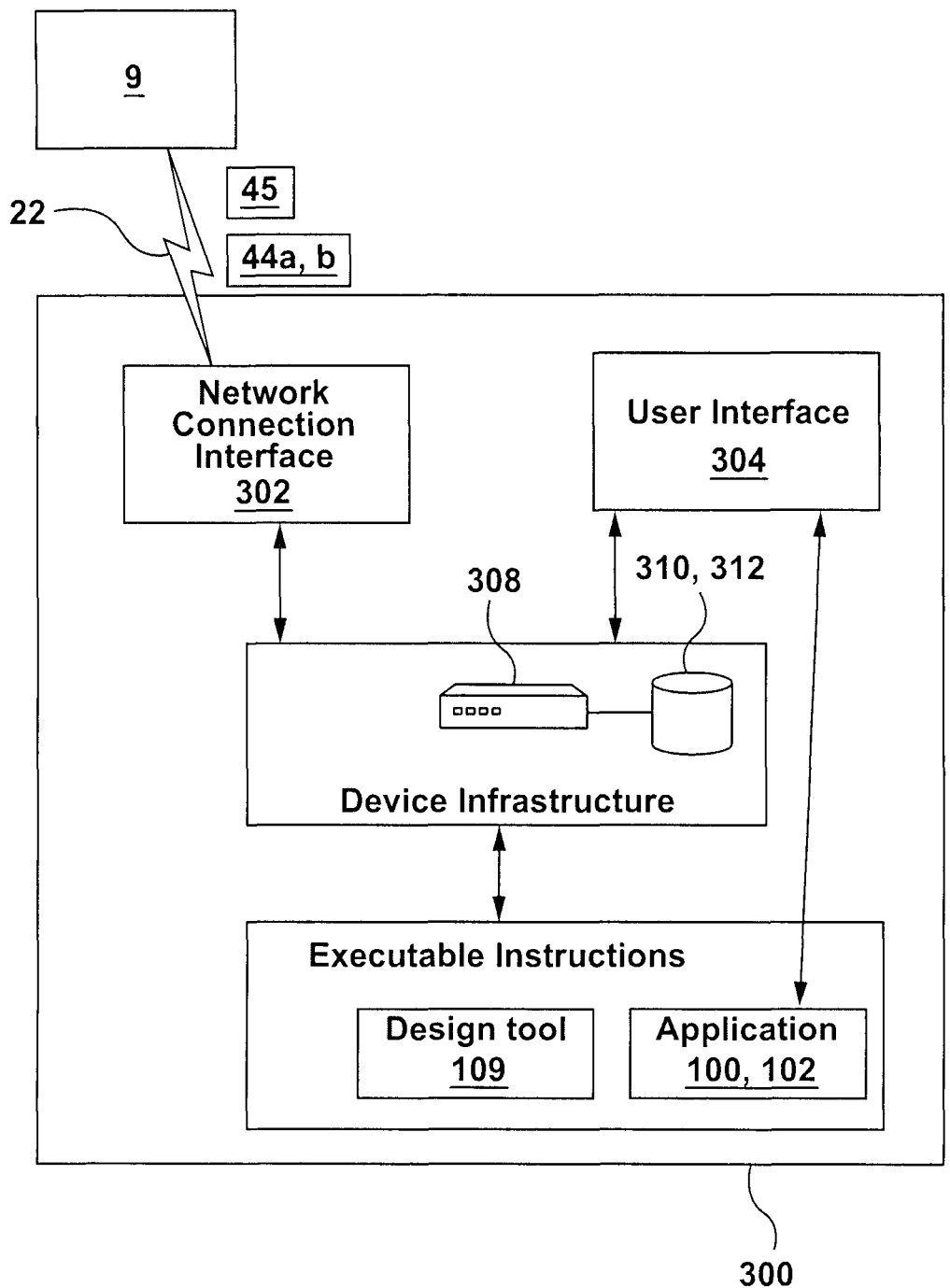
FIG. 13 is a block diagram of an example data processing system of the system of FIG. 10.

As further described below, the data 44a can be collected from the wearer 8 using the sensor platform 9 (e.g. ECG readings, temperature readings, etc.) and can also be applied to the wearer 8 (generating heat, generating vibration, generating pressure, etc. for application to the skin/body of the wearer 8) based on the biometric data 44b received by the wearer 8 (via and processed by the garment computer device 14) from a networked user 6 operating device 60 (e.g. a version of data processing system 300 as shown in FIG. 13).

Dual Garment Example for Both Wearer 8 and User 6

In the case where the user 6 also is wearing a garment containing a sensor platform 9, as further described below, the biometric data 44a can be collected from the user 6 using the sensor platform 9 (e.g. ECG readings, temperature readings, etc.) and can also be applied to the user 6 (generating heat, generating vibration, generating pressure, etc. for application to the skin/body of the user 6) based on the biometric data 44b received by the user 6 (via and processed by a garment computer device 60) from a networked wearer 8 operating device 14. It is also recognized that the user 6 (and/or wearer 8) can generate the biometric data 44a,b using functionality (e.g. user interface selection(s)) of their device application 100,102, rather than using sensors of their sensor platform 9 of their respective garment 11. In this example, the biometric data 44a,b is communicated in a bidirectional fashion over the communications network 22 between the user 6 and the wearer 8. One example is where the wearer 8 can be a patient of a doctor (i.e. the user 6), which in this case the user 6 may interact directly with their device application 102 to generate and send a set of commands 45 for receipt and application to the body of the wearer 8 via the wearer's 8 sensor platform 9 (e.g. the user 6 generates and sends remotely a pressure and heat command representative of the user's hand pressure on a body portion—e.g. leg—of the wearer 8). The sensor platform 9 of the wearer 8 would receive and thus replicate (i.e. apply) the set of commands 45 of the user 6, i.e. generate the heat and pressure of the set of commands 45 on the body of the wearer 8 via activation of the sensor platform 9 (of the wearer's garment 11) accordingly. In this case the user 6 can interact directly with their sensor platform 9 (as interpreted by their device application 102 such as pressing on or otherwise physically touching one or more sensors 12,36 of their sensor platform 9) to generate and send the set of commands 45 for receipt and application to the body of the wearer 8 via the wearer's sensor platform 9 (e.g. the user 6 generates and sends remotely a pressure and heat command representative of the user's hand pressure on a body portion—e.g. leg—of the user 6 via activation of their sensor platform 9). In turn, the sensor platform 9 of the wearer 8 would receive and thus replicate (i.e. apply) the set of commands 45 of the user, i.e. generate the heat and pressure of the set of commands 45 generated from operation of the sensor platform 9 of the user 6 on the body of the wearer 8 via activation of the sensor platform 9 (of the wearer's garment 11) accordingly.

For example, the wearer 8 may be a friend/family of the user 6 being, which in this case the user 6 may interact directly with their device application 102 to generate and send a set of commands 45 for receipt and application to the body of the wearer 8 via the wearer's sensor platform 9 (e.g. the user 6 generates and sends remotely a pressure and heat command representative of the user's hand pressure on a body portion—e.g. leg—of the wearer 8). The sensor platform 9 of the wearer 8 would receive and thus replicate (i.e. apply) the set of commands 45 of the user 6, i.e. generate the heat and pressure of the set of commands 45 on the body of the wearer 8 via activation of the sensor platform 9 (of the wearer's garment 11) accordingly. As discussed below, the command(s) 45 can be representative of certain physical actions or emotions (e.g. happiness, a hug, a pat on the back, a backrub, a gentle sense of warmth near the heart, etc.). As further described below the wearer 8 and the user 6 can communicate biometric data 44a,b (e.g. representative of biosignals as well as that of sense data—e.g. any or all of five senses including sight, smell, taste, touch and hearing) bidirectionally with one another over the network 22.

The sensor platform 9 can be utilized to collect as well as to express biosignals (represented by the data 44a,b), which can be identified by the wearer/user of the devices 14,60 as a sensory language for intercommunication over the network 20 between the devices 14,60. For example, the wearer 8 can instruct the computer device 14 (or paired device 40) to generate one or more commands 45 (see FIG. 10) containing data 44a collected as sensory output of the wearer 8 and sent over the network 22 as a sensory input as data 44b to a corresponding sensor platform 9 of the user 6. For example, the user 6 can instruct the computer device 60 (or paired device 40) to generate one or more commands 45 (see FIG. 10) containing data 44a collected as sensory output of the user 6 and sent over the network 22 as sensory input as data 44b to a corresponding sensor platform 9 of the wearer 8. It is recognized that the commands 45 can be part of a synchronous (command eliciting response) or an asynchronous (command with no expected response) communication between the wearer 8 and user 6 over the network 22.

It is also recognized that the term command 45 can also be replaced intraoperatively with the term notification 45, such that the data 44a,b being sent between the wearer 8 and user 6 can be regarded as a notification 45 of the sender's physical/emotional state, e.g. the wearer 8 sends a notification 45 of their happiness—expressed as a sense of warmth for application via sensors 12 as warmth adjacent to a selected body part of the user 6—e.g. heart via their sensor platform 9, e.g. the wearer 8 sends a notification 45 of their pain—expressed as a sense of vibration for application via sensors 12 as vibration adjacent to a selected body part of the user 6—e.g. leg via their sensor platform 9 and/or user interface of their device 60).

The communication of commands/responses 45 between the wearer 8 and user 6 can be by way of a third party application service 101 of a server 41, for example a medical service 101 registered with by both the wearer 8 (via respective device 14,40) as patient and user 6 (via respective device 60,40) as medical practitioner. The communication of commands/responses 45 between the wearer 8 and the user 6 can be by way of the third party application service 101 of server 41, for example a social media service 101 (e.g. Facebook™, Twitter™, Linkin™, etc.) registered with by both the wearer 8 (via respective device 14,40) as friend/family/colleague and user 6 (via respective device 60,40) as reciprocal friend/family/colleague.

Single Garment Example of Wearer 8 with Interaction with Network Device 60 of User 6

In the case where the user 6 only has a network device 60 in communication with the wearer 8 (e.g. over the communications network 22 directly with the computing device 14 and/or via an intermediary networked device 40 of the wearer 8), the biometric data 44a can be collected from the wearer 8 using the sensor platform 9 (e.g. ECG readings, temperature readings, etc.) and can also be applied as biometric data 4b to the wearer 8 (generating heat, generating vibration, generating pressure, etc. for application to the skin/body of the wearer 8) based on the biometric data 44b received by the wearer 8 (via and processed by a garment computer device 40) from a networked user 8 operating their network device 60. It is recognized that the user 6 can generate the biometric data 44b using functionality (e.g. user interface selection(s)) of their device application 102. In this example, the biometric data 44a,b is communicated in a bidirectional fashion over the communications network 22 between the user 6 and the wearer 8. One example is where the wearer 8 can be a patient of a doctor (i.e. the user 6), which in this case the user 6 may interact directly with their device application 102 to generate and send a set of commands 45 for receipt and application to the body of the wearer 8 via the wearer's 8 sensor platform 9 (e.g. the user 6 generates and sends remotely a pressure and heat command representative of the user's hand pressure on a body portion—e.g. leg—of the wearer 8). The sensor platform 9 of the wearer 8 would receive and thus replicate (i.e. apply) the set of commands 45 of the user 6, i.e. generate the heat and pressure of the set of commands 45 on the body of the wearer 8 via activation of the sensor platform 9 (of the wearer's garment 11) accordingly. In this case the user 6 can interact directly with their device application 102 to generate and send the set of commands 45 for receipt and application to the body of the wearer 8 via the wearer's sensor platform 9.

For example, the wearer 8 may be a friend/family of the user 6 being, which in this case the user 6 may interact directly with their device application 102 to generate and send a set of commands 45 for receipt and application to the body of the wearer 8 via the wearer's sensor platform 9 (e.g. the user 6 generates and sends remotely a pressure and heat command representative of the user's hand pressure on a body portion—e.g. leg—of the wearer 8). The sensor platform 9 of the wearer 8 would receive and thus replicate (i.e. apply) the set of commands 45 of the user 6, i.e. generate the heat and pressure of the set of commands 45 on the body of the wearer 8 via activation of the sensor platform 9 (of the wearer's garment 11) accordingly. As discussed below, the command(s) 45 can be representative of certain physical actions or emotions (e.g. happiness, a hug, a pat on the back, a backrub, a gentle sense of warmth near the heart, etc.). As further described below the wearer 8 and the user 6 can communicate biometric data 44a,b (e.g. representative of biosignals as well as that of sense data—e.g. any or all of five senses including sight, smell, taste, touch and hearing) bidirectionally with one another over the network 22.

The sensor platform 9 can be utilized to collect as well as to express biosignals (represented by the data 44a,b), which can be identified by the wearer/user of the devices 14,40,60 as a sensory language for intercommunication over the network 20 between the devices 14,40,60. For example, the wearer 8 can instruct the computer device 14 (or paired device 40) to generate one or more commands 45 containing data 44a collected as sensory output of the wearer 8 and sent over the network 22 to the network device 60 of the user 6. In response, the user 6 can instruct the computer device 60 to generate one or more commands 45 (see FIG. 10) containing data 44b and send over the network 22 as sensory input as data 44b to a corresponding sensor platform 9 of the wearer 8. It is recognized that the commands 45 can be part of a synchronous (command eliciting response) or an asynchronous (command with no expected response) communication between the wearer 8 and user 6 over the network 22.

It is also recognized that the term command 45 can also be replaced intraoperatively with the term notification 45, such that the data 44a,b being sent between the wearer 8 and user 6 can be regarded as a notification 45 of the sender's physical/emotional state, e.g. the wearer 8 sends a notification 45 of their happiness—expressed as a sense of warmth for application via sensors 12 as warmth adjacent to a selected body part of the user 6—e.g. heart via their sensor platform 9, e.g. the wearer 8 sends a notification 45 of their pain—expressed as a sense of vibration for application via sensors 12 as vibration adjacent to a selected body part of the user 6—e.g. leg via their sensor platform 9 and/or user interface of their device 60).

The communication of commands/responses 45 between the wearer 8 and user 6 can be by way of a third party application service 101 of a server 41, for example a medical service 101 registered with by both the wearer 8 (via respective device 14,40) as patient and user 6 (via respective device 60,40) as medical practitioner. The communication of commands/responses 45 between the wearer 8 and the user 6 can be by way of the third party application service 101 of server 41, for example a social media service 101 (e.g. Facebook™, Twitter™, Linkin™, etc.) registered with by both the wearer 8 (via respective device 14,40) as friend/family/colleague and user 6 (via respective device 60,40) as reciprocal friend/family/colleague.

Single Garment Example of Wearer 8 with Interaction with Network Device 14,40 of Wearer 8

In the case where the wearer 8 has a network device 40 in communication with the computing device 14, the biometric data 44a can be collected from the wearer 8 using the sensor platform 9 (e.g. ECG readings, temperature readings, etc.), can be processed by the device(s) 14,40 and then the processed result applied as biometric data 44b to the wearer 8 (generating heat, generating vibration, generating pressure, etc. for application to the skin/body of the wearer 8) based on the biometric data 44b received by the wearer 8 (via and processed by sensor platform 9). It is recognized that the application 100 (of the network device 40) can generate the biometric data 44b using functionality (e.g. user interface selection(s)) of the device application 100. In this example, the biometric data 44a,b is communicated in a bidirectional fashion over the communications network 22 between the sensor platform 9 and the network device 40 (e.g. via the computing device 14 used as a data collection and data application controller of the sensors/actuators 12 of the sensor platform 9). The application 100 can be configured to automatically respond to the received biometric data 44a via a predefined set of instructions, e.g. biometric data 44a representative of a wearer body temperature under a predefined minimum would automatically generate heat commands 45 as the biometric data 44b for subsequent sending to and consumption by the heat actuators 12 of the sensor platform 9 of the wearer 8).

Sensor/Platform Types

Figure 2:
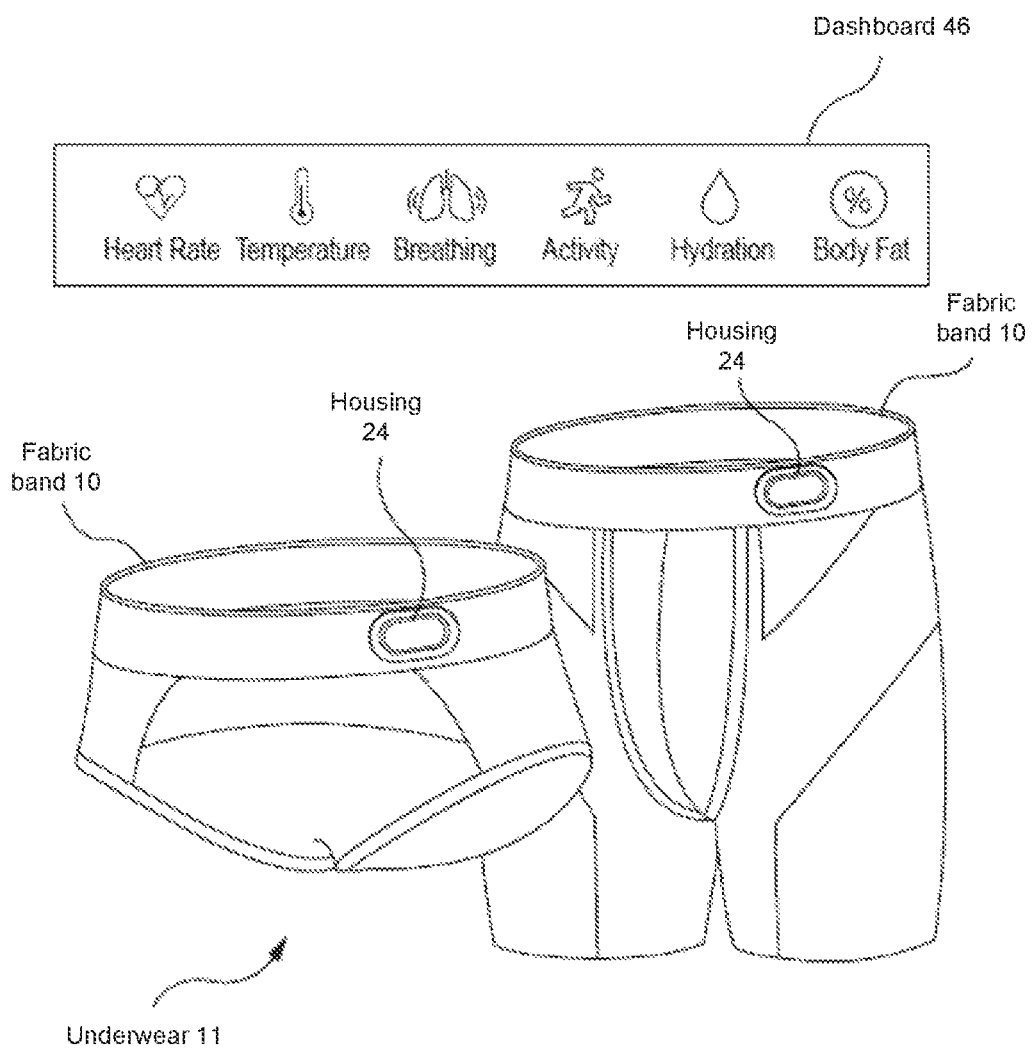
FIG. 2 is a view of the band shown in FIG. 1a incorporated into an article of clothing.

It is recognized that selected ones of the sensors 12 of the sensor platform 9 can be unidirectional (i.e. used to collect biometric signals representing the data 44a from the wearer/user or used to apply biometric signals representing the data 44b to the wearer/user), bidirectional (i.e. used to both collect biometric signals representing the data 44a from the wearer/user and apply biometric signals representing the data 44b to the user/wearer). As discussed, functionality of the garment 11 with resident sensor platform 9 can be described with relation to the wearer 8, however recognizing that similar functionality can be also of the respective garment 11 and sensor platform 9 of the user 6. The body part of the wearer 8 (i.e. also of the user 6) adjacent the sensor platform 9 can be covered by the garment 11, which cover all or part of body part(s) such as but not limited to: waist or abdomen; limb such as a leg or arm; torso/trunk; buttocks; foot or ankle; wrist or hand; and/or head. The fabric band 10, as one example of the sensor platform 9, can be provided as a stand-alone article or can be combined/combined into an article of clothing such as but not limited to: underwear 11 (see FIG. 2—such as but not limited to any type of undergarment including jockey shorts, panties, undershirts, and bras); socks, limb bands (e.g. knee band—see FIG. 1b); shirt (e.g. undershirt); etc. In terms of combined into an article of clothing (i.e. garment 11), the band 10 can be formed as an integral component of the interlacing of the fibres making up the garment 11. The fabric of the body of the band 10 (e.g. sensor platform 9) can be comprised of interlaced resilient fibres (e.g. stretchable natural and/or synthetic material and/or a combination of stretchable and non-stretchable materials). It is also recognized that sensor platform 9 (e.g. band 10) can be positioned on/in one or more locations of the garment 11, or can be the garment itself.

Referring again to FIG. 1a, provided as distributed about the band 10, e.g. mounted on an interior surface 111 (i.e. inward facing towards the body of the wearer), are a series of sensors/electrodes 12 including ECG sensors 12a, bio impedance sensors 12b, and strain gauge sensors 12c. It is recognized that the sensors 12 can be composed of Electroactive polymers, or EAPs, and/or woven or knit plurality of conductive fibres constructed in a sensor/electrode configuration (e.g. a patch). The sensors 12 can also include a position/location sensor in order to be able to detect the physical location of the wearer/user (e.g. location within or outside of their home/building).

The sensor platform 9 can be utilized to collect as well as to express biosignals (represented by the data 44a,b), which can be identified by the wearer/user of the devices 14,60 as a sensory language for intercommunication over the network 20 between the devices 14,60. For example, the wearer 8 can instruct the computer device 14 (or paired device 40) to generate one or more commands 45 (see FIG. 10) containing data 44a collected as sensory output of the wearer 8 and sent over the network 22 as a sensory input as data 44b to a corresponding sensor platform 9 of the user 6. It is also recognized that the term command 45 can also be replaced intraoperatively with the term notification 45, such that the data 44a,b being sent between the wearer 8 and user 6 can be regarded as a notification 45 of the sender's physical/emotional state, e.g. the wearer 8 sends a notification 45 of their happiness—expressed as a sense of warmth for application via sensors 12 as warmth adjacent to a selected body part of the user 6—e.g. heart via their sensor platform 9, e.g. the wearer 8 sends a notification 45 of their pain—expressed as a sense of vibration for application via sensors 12 as vibration adjacent to a selected body part of the user 6—e.g. leg via their sensor platform 9 and/or user interface of their device 60).

Example Sensors 12

Shape Shifting Alloy Yarn (i.e. fibre) sensor 12 can be based on development on shape memory fine alloy based yarn, in order to control and dictate shape shifting properties of the sensor 12 through an annealing process applied to the yarn individually and/or to the woven/knit sensor 12 (e.g. patch or garment 11 portion thereof) as a whole. The explored annealing process provided improvements to the ductility, reduction in the hardness and made the alloy yarn more malleable for knitting/weaving. Twisting or breading of the annealed alloy fibres with conventional yarns (such as nylon or polyester) can also be done in order to create a multi-filament yarn which can make it easier to employ in knitting structures as the sensors 12. The Alloy Yarn (i.e. fibre) sensor 12 can also be subjected to combination effects of heat annealing and strain annealing in order to provide for functionality of the respective sensor 12 in shape forming/retaining/shifting properties. As such, one example use of the sensor 12 incorporating the alloy fibres is for providing input and/or output of sensory touch of the wearer/user, either from or to the wearer/user via the commands 45. In parallel, the control of the shape shifting annealed alloys fibres can be done through laser etching, to create a range of shape shifting profiles along a single fibre strand (or combination of strands), as desired. Also, braiding of the shape shifting alloy fibres can create sensor 12 structure which exhibits a stronger (i.e. predefined) contraction/expansion that could lead to greater (i.e. defined) shape shifting on garments 11 via the sensor platform 9.

A thermal yarn fibre for the sensors 12 can be a resistive yarn which has the ability to generate/conduct heat via the application of a current (or generation of a current) through the yarn, i.e. as sensory output/input of the wearer/user implemented by the corresponding application 100,102 of the device 14,60. The resistance profile of the yarn for the sensor 12 can be adjusted such that it can provide a variety of temperature profiles, as selectable via the application 100,102. The developed resistive yarns can be wash tested and certified for daily/regular use such that there can be minimal changes in the resistive properties, i.e. resistive property stability, which could otherwise affect the heating profiles and power requirements of the resistive yarn of the sensors 12. However, it is also recognized that the applications 100,102 could be configured to compensate for any degradation in the resistive yarns/sensors 12, as desired. As such, one example use of the sensor 12 incorporating the thermal fibres is for providing input and/or output of sensory touch of the wearer/user, either from or to the wearer/user via the commands 45.

Piezoelectric Yarns for the sensors 12 can be for housing a plurality of sensory properties (e.g. shape shifting, heat, etc.) in a single filament/fibre. For example, utilization of melting yarns in the sensors 12 can serve as an insulation between active segments (e.g. conductive for heat and/or electricity) of the piezoelectric yarn, all extruded as a single filament. For example, it is envisioned that these yarns will give the ability of producing movement through a new medium on textiles, either from or to the wearer/user via the commands 45.

Electromagnetic Yarns for the sensors 12 can be used to produce haptic feedback through a magnetic field, e.g. as a sensory input or output. For example, through a coil like knit structure of the sensor 12 and the employment of ferromagnetic yarn/fibres, the sensor platform 9 would have the ability to generate vibrational movements either from or to the wearer/user via the commands 45.

Electrical Stimulation fibres of the sensors 12 can provide/receive a seamless and pain-inhibited electrical pulse to/from the skin as a new modality of sensation via textiles via the sensor platform 9. The electrical simulation proficient yarn/fibres can be incorporated in garments 11 on desired locations via the sensor platform 9 and operated via a low (i.e. appropriate) current signal administered via the application 100,102 and associated data processing system. For example, electrical pulses can be transmitted to the skin, which can invoke a tactile sensation, either from or to the wearer/user via the commands 45.

As discussed, the combination of any of the mentioned sensor/actuation 12 modalities can be employed in generation/sending and receipt/processing of the commands 45 using the sensor platform 9. As such, any of shape shifting alloy, thermal yarn, piezoelectric yarn, electro-magnetic yarn, electrical stimulation yarn can be used in the sensors 12 and therefore facilitate giving the wearer/user the ability to send and receive physical cues from each other. The physical cues are defined as the commands/responses 45 for representing physical-based (e.g. a hug) and/or emotional-based (e.g. a smile, happiness, excitement) as sensory biosignals for generation/sending and receipt/application via the data 44a,b. It is recognized that use of the commands 45 can bring about a new series of human interactions via the sensor platform(s) 9, expressed as social intricacies and/or transfer of human sensory output/input through a textile medium (i.e. the sensor platform 9 incorporated as or otherwise in the garment 11.

The sensors 12 can be composed of Electroactive polymers, or EAPs, which are polymers that exhibit a change in size or shape when stimulated by an electric field. EAPS could also exhibit a change in electrical field if stimulated by mechanical deformation. The most common applications of this type of material are in actuators and sensors. A typical characteristic property of an EAP is that they will undergo deformation while sustaining forces. For example, EPDM rubber containing various additives for optimum conductivity, flexibility and ease of fabrication can be used as a sensor 12 material for measuring electrode impedance measured on human skin of the wearer. Further, EAPs may be used to measure ECG as well as measuring deformation (i.e. expansion of the waist and therefore breathing can be inferred from EAPs). ECG can be measured using surface electrodes, textile or polymer, as desired.

These electrodes 12 can be capable of recording biopotential signals such as ECG while for low-amplitude signals such as EEG, as coupled via pathways 30 with an active circuit of the electrical components 15 within the housing 24. The ECG sensors 12a can be used to collect and transmit signals to the computer processor 16 reflective of the heart rate of the wearer. As such, it is recognized that the electrodes as sensors 12 can be composed of conductive yarn/fibres (e.g. knitted, woven, embroidery using conductive fibres—e.g. silver wire/threads) of the band 10, as desired.

In terms of bioelectrical impedance, these sensors 12a,b and their measurements can be used in analysis (BIA) via the processor 16 and memory 18 instructions for estimating body composition, and in particular body fat. In terms of estimating body fat, BIA actually determines the electrical impedance, or opposition to the flow of an electric current through body tissues of the wearer interposed between the sensors 12 (e.g. 12a,b), which can then be used to estimate total body water (TBW), which can be used to estimate fat-free body mass and, by difference with body weight, body fat.

In terms of strain sensing, these sensors 12c can be operated as a strain gauge to take advantage of the physical property of electrical conductance and its dependence on the conductor's geometry. When the electrical conductor 12c is stretched within the limits of its elasticity such that it does not break or permanently deform, the sensor 12c will become narrower and longer, changes that increase its electrical resistance end-to-end. Conversely, when the sensor 12c is compressed such that it does not buckle, the sensor 12c will broaden and shorten, changes that decrease its electrical resistance end-to-end. From the measured electrical resistance of the strain gauge, via the power 28 that is administered to the sensors 12 via the computer processor 16 acting on stored 18 instructions, the amount of induced stress can be inferred. For example, a strain gauge 12c arranged as a long, thin conductive fibres in a zig-zag pattern of parallel lines such that a small amount of stress in the direction of the orientation of the parallel lines results in a multiplicatively larger strain measurement over the effective length of the conductor surfaces in the array of conductive lines—and hence a multiplicatively larger change in resistance—than would be observed with a single straight-line conductive wire. In terms of location/structure of the strain gauge 12c, the strain gauge can be located around the circumference of the band 10. A further embodiment is where the strain gauge 12c is located in a portion of the circumference, for example in a serpentine arrangement, positioned in a front 52 portion (positioned adjacent to the front of the wearer) of the band 10. The strain gauge 12c can be configured for sensing in the k Ohm range.

In terms of temperature sensor 12d, this sensor is used to measure the dynamic body temperature of the wear. For example, the temperature sensor 12d can be a thermistor type sensor, which is a thermally sensitive resistors whose prime function is to exhibit a large, predictable and precise change in electrical resistance when subjected to a corresponding change in body temperature. Examples cam include Negative Temperature Coefficient (NTC) thermistors exhibiting a decrease in electrical resistance when subjected to an increase in body temperature and Positive Temperature Coefficient (PTC) thermistors exhibiting an increase in electrical resistance when subjected to an increase in body temperature. Other temperature sensor types can include thermocouples, resistance thermometers and/or silicon bandgap temperature sensors as desired. It is also recognized that the sensors 12 can include haptic feedback sensors that can be actuated via the computer processor 16 in response to sensed data 44a,b processed onboard by the processor 16 and/or instructions received from a third party device 60 or the wearer (operator of the computer device 40) via an interface 20. Another example of temperature sensors 12d is where thermocouples could be knitted into the band 10 fabric using textile and coupled directly to the body of the wearer through close proximity/contact in order to get more accurate temperature readings. Device 14,40,60 Interaction with Wearer 8 and User 6

Referring again to FIG. 1, also positioned on the band 10 (i.e. sensor [platform 9) or otherwise coupled thereto, for example on an exterior surface 13 (i.e. outward facing from the wearer), is series of electrical components 15 including a computer device 14 (see FIG. 3) including a computer processor 16, a memory 18 for executing stored instructions for receiving and processing of data obtained from the sensors 12, as well as communicating via a network interface 20 with a network 22 (e.g. Wi-Fi, Bluetooth, attached wired cable, etc.) as well as sending and receiving electrical signals from the sensors 12. The processor 16, memory 18 and network interface 20 are mounted on a printed circuit board 26, which is housed in a housing 24 attached to the band 10. Also connected to the PCB 24 is a temperature sensor 12d for measuring a body temperature of the wearer 8. Also mounted in the housing is a power supply 28 (e.g. battery) for powering the various electrical components 15 within the housing 24 as well as the sensors 12a,b,c external to the housing 24, connected via conductive communication pathways 30 (e.g. wires—see FIG. 1—woven into the fabric weave/knit of the band 10 textile). The pathways 30 can be coupled to the sensors 12 via use of a conductive grommet, as desired. Also provided is a series of motion sensors 36 (e.g. accelerometer(s) and gyroscopes) for determining movements of the wearer, including posture as further described below. The sensors 12 can also be provided as speaker/microphone (e.g. for auditory signals/communication with the wearer), illumination sensors (e.g. LEDS—for visual signals/communication with the wearer) and haptic/vibrations sensors (e.g. actuators—for motion/touch signals/communication with the wearer).

Referring again to FIGS. 2 and 3, the processor 16 (acting on stored 18 instructions) can transmit the collected data 44a (in raw format and/or in preprocessed format from the sensors 12) to an external computer device 40 (e.g. smartphone or other desktop application) for viewing and/or further processing of the sense data. For example, the device 40 application can display the sensed data 44a in a dashboard type format 46 on a display 42 (or other type of GUI interface) for viewing by the wearer (or by another person other than the wearer that has been provided access to the data 44a). For example, the sensed data 44a can be provided in a dashboard format indicating real-time (or other selected dynamic periodic frequency) of: body temperature for indicating fluctuations in skin temperature; gyroscope/accelerometer measurements for indicating amount/degree of physical activity (i.e. via sensed motion) of the wearer as well as contributing via gyroscope readings of wearer posture (for example in the case where the band 10 is positioned at the waist of the wearer) as well as determined calculation of number of calories expended; strain gauge measurements (e.g. via conductive yarn) in order to indicate real-time breathing of the wearer as the band 10 expands and contracts as well as the ability to differentiate strain degree contributing to posture angle (i.e. band and associated strain sensor 12c with change in length as the posture of the wearer changes due to bending at the waist—in the case of the underwear 11 example of FIG. 2); real-time heart rate measurements based on sensed ECG data using the sensors 12a; and real-time hydration/body fat measurements based on galvanic sensing using the sensors 12b (and optionally 12a as further described below).

It is recognized that multiple sources of sensed data (e.g. temperature sensor 12d with activity/motion sensors 36 can be used in an algorithm stored in memory 18 to calculate calories expended based on activity combined with body temperature). Other combinations of sensed data 44a types can include combinations such as but not limited to: heart rate with activity data; heart rate with activity data with temperature; activity data with bio impedance data; strain gauge for breathing rate data determination with activity data and heart rate data for determination of exertion levels; etc. It is also realized that combinations of sensor type readings can be used by the computer processor 16 to determine exercise activity type being performed by the wearer, based on computer models of activity type with typical sensor data, for example gradual changes in body posture with detected lower levels of heart rate and breathing could be indicative of a wearer practicing yoga. A further type of multiple sensed data usage can be for accelerometer and gyroscope data, such that both can be used or one can be used and the other discounted during determination of a selected metric of the dashboard 46. For example, in the case of the band 10 being situated at the waist of an overweight person, the "off-vertical" reading of the gyroscope would not be indicative of a bent posture (from the vertical), rather due to the folded waistband due to body composition. As such, the degree of gyroscope readings would be discounted from the calculation of the posture determination.

Referring again to FIG. 1, the location of the sensors 12 a,b can be such that they are positioned in pairs on either side of a centerline 50, in order to position an appropriate amount of body mass between the sensors 12a,b as well as providing an appropriate conductive path through the body of the wearer (e.g. cross body measurement). It is also recognized that placement of the sensors 12a,b can be preferred in body regions where muscle noise (actions of muscles can introduce signal noise into the adjacent sensors 12) is minimized. As such, the sensors 12a,b can be positioned in the band 10 in a location for positioning adjacent to the hip and/or the kidney of the wearer in the case where the band 10 is positioned at the waist. It is recognized that positioning the sensors 12a,b in the band 10 in order to be adjacent to either hip of the wearer, i.e. both sensors 12a,b of the pair to one side of the centerline 56 of the band 10, would provide for a lower signal amplitude/quality when wearer activity is subdued (e.g. resting) however would also advantageously provide an increases signal quality when the wearer is active (as the presence of utilized muscle mass adjacent to the hip region is minimal as compared to other regions about the waist).

It is also recognized that location of the sensors 12a,b can be positioned to either side of the centerline 50 running front to back rather than to either side of the centerline 56 running side to side (of the wearer), as the separation distance for the typical wearer is greater side to side rather than front to back (i.e. wider between hips verses between spine and belly button).

Further, one example option for the sensor configuration is a 4-electrode ECG sensor configuration. Cost of such an ECG design can be a factors however the design could potentially give better signal performance. The theory behind the four sensor ECG design is that the processor 16 can switch between each sensor pair (of the multiple pair ECG sensor configuration) to find the one with the best signal quality and use that one during sensed movement of the wearer.

Referring again to FIG. 3, the processor 16 and associated stored 18 instructions can be used to determine (based on received sensor 12 readings) bio impedance values by utilizing both of the ECG sensors 12a and the sensors 12b at the same time. This is advantageous as EGC sensing (using sensors 12a) cannot occur at the same time as bio impedance sensing (using sensors 12b), as signal amplitude generated by the sensors 12b oversaturates the EGC sensors 12a. As such, it is recognized that the processor 16 cycles between ECG readings and bio impedance readings (i.e. these readings are done sequentially rather than in parallel). As such, the processor instructs power to both the sensors 12a,b on one side of the centerline 50 as drivers and both the sensors 12a,b on the other side of the centerline 50 as collectors during taking of bio impedance readings. As such, it is recognized that the positioning of the sensor pair 12a and the sensor pair 12b can be symmetrical about the centerline(s) 50,56.

Figure 3:
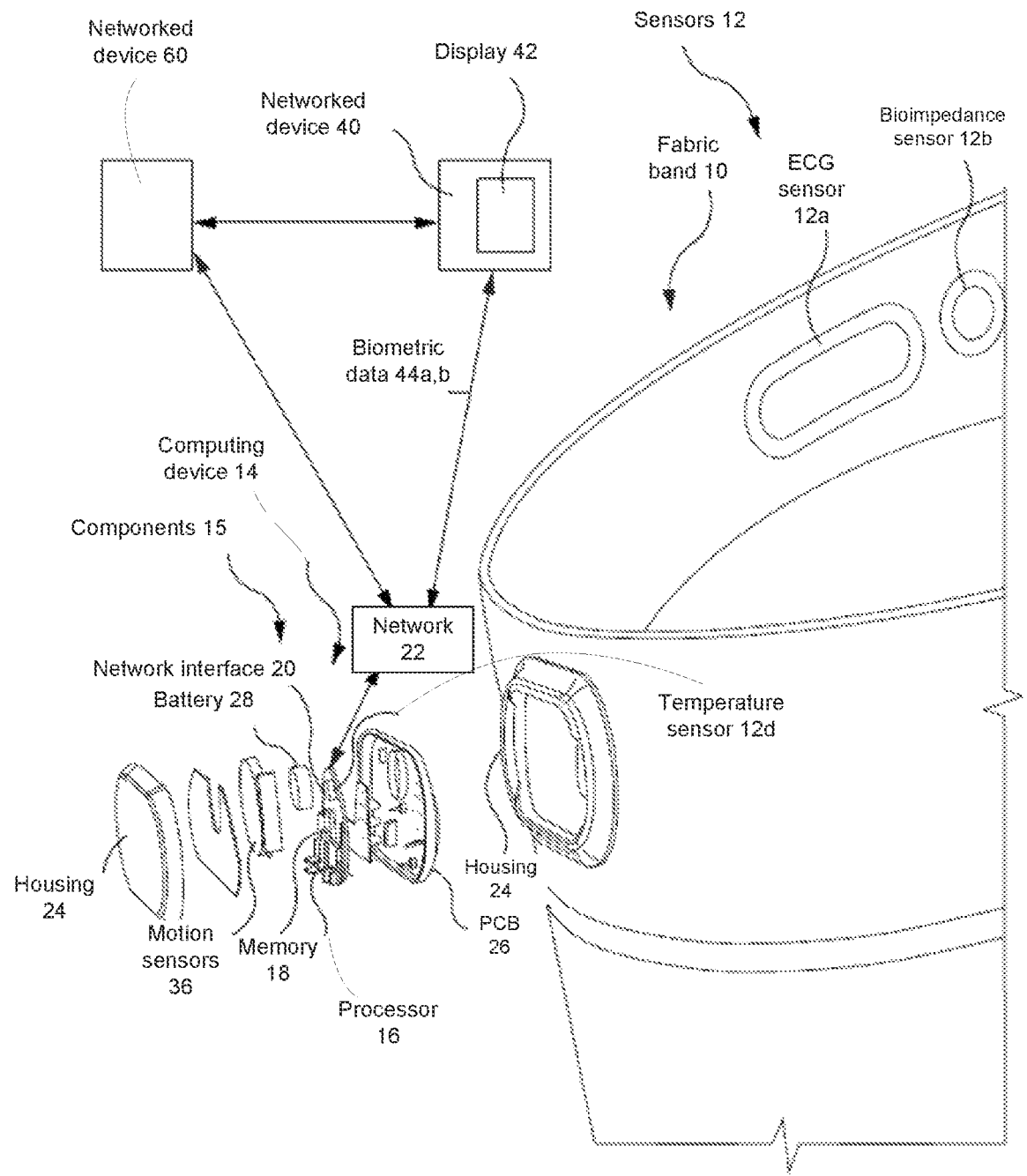
FIG. 3 shows an embodiment of the band shown in FIG. 1a with associated electrical components.

Referring to FIGS. 3 and 4, the computer device 14 can be used to send/receive the sensed data 44a to the off band computer device 40, which can then use its own customized applications 43 (e.g. 100,102) to process the sensed data 44a to inform the wearer/user of their physical/mental state on potential adaptations/changes that can be actively done by the wearer/user. For example, the application 43 can report sensed data 44a pertaining to a combination of temperature and activity over time as an indicator of the quality of sleep of the wearer. Further, the application 43 can notify the wearer of a determined emotional state of the wearer (e.g. based on a combination of breathing data and activity data—with optional ECG data) as well as continued monitoring of the data combination to inform the wearer whether steps taken by the wearer are positively influencing the determined emotional state. Further, the application 43 can track and report on the degree as well as quality/nature of the wearer's activity, for example based on a combination of strain gauge data and activity data. Further, the application 43 can interact with other external computer networked devices 60 (see FIG. 3) of the user 6, as well as other networked devices 60 providing predefined functionality to the user 6/wearer 8, such as but not limited to music systems, heating system, lighting systems, etc. in response to a determined mood and/or temperature of the wearer based on a combination of sensed data (e.g. activity, heartrate, etc.). For example, the commands 45 of the user 6, wearer 8 can be sent to a networked device 60 of the wearer 8, user 6 as a direction to change the functionality of the device 60.

Figure 5:
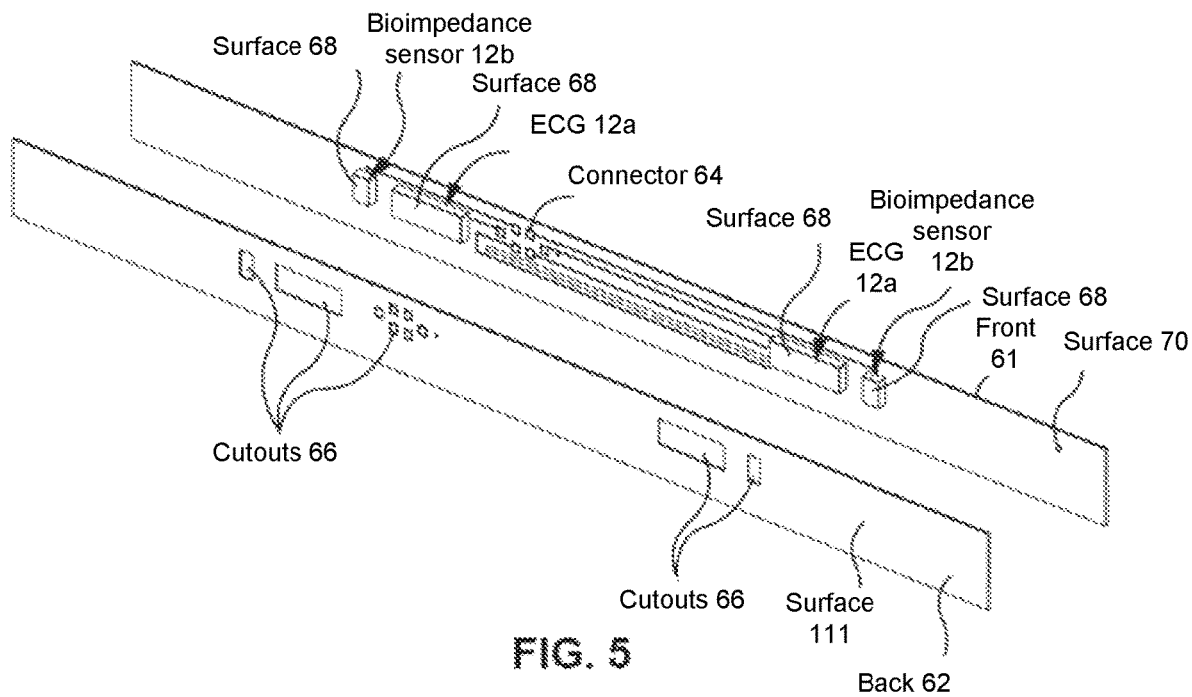
FIG. 5 shows a front perspective view of a further embodiment of the band of FIG. 1.
Figure 6:
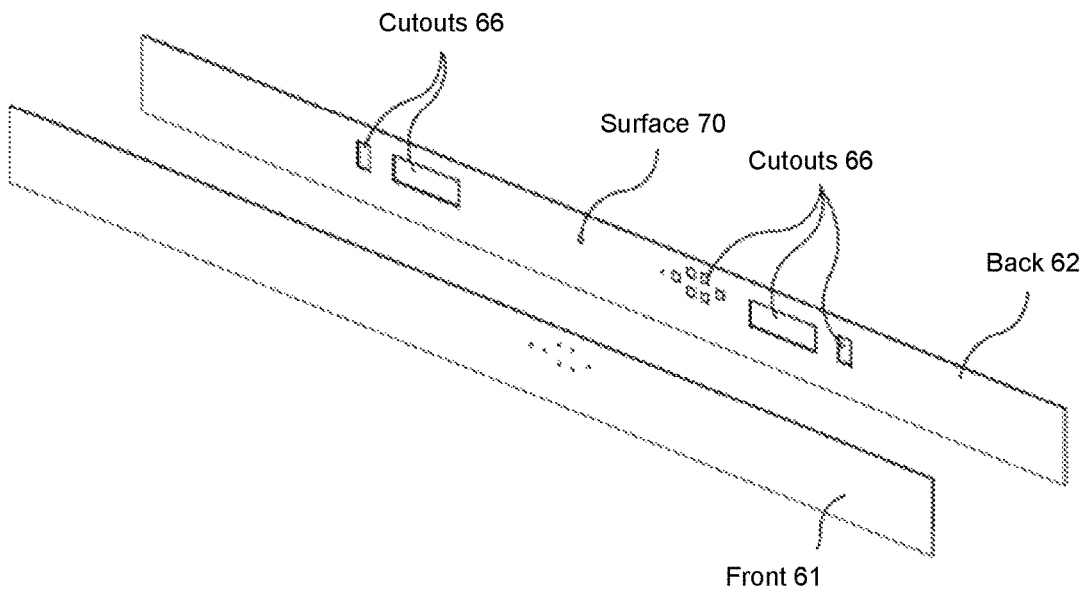
FIG. 6 shows a rear perspective view of the further embodiment of FIG. 5.

Referring to FIGS. 5 and 6, shown is an alternative embodiment of the band 10, in exploded view. In particular, the band 10 is composed of a front band portion 61 and a back band portion 62, such that the portion 61 has sensors 12a,b with communication pathways 30 electrically connecting the sensors 12a,b to respective connectors 64 (which connect to respective connector portions of the PCB 26 (see FIG. 3), in order to electrically couple the sensors 12a,b to the network interface 20). The band portion 62 has cutouts 66 in order for the sensors 12a,b to be received in the cutouts 66 when the band portions 61,62 are assembled with one another (e.g. coupled together for example by stitching via adjacently places surfaces 70), thus providing for surfaces 68 of the sensors 12a,b to become in contact with the skin of the wearer, as the surface 111 is for contact with the skin. It is recognized that the electrically conductive pathways 30 can be electrically conductive fibres interlaced with electrically insulative fibres comprising the material of the band portion 61.

Figure 7:
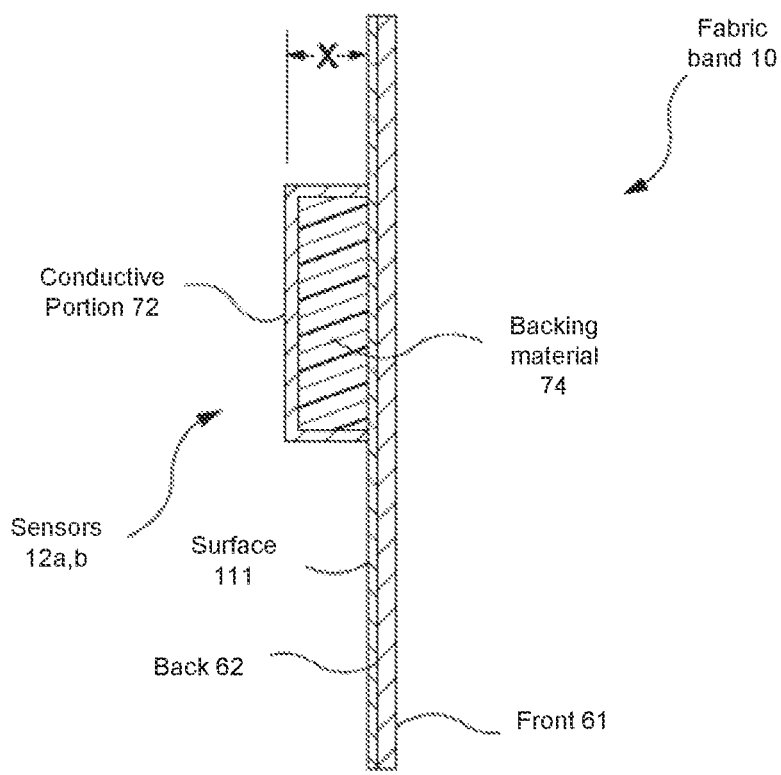
FIG. 7 shows a side view of the sensors mounted on the band of FIG. 5.

Referring to FIG. 7, shown is an example side view of one of the sensors 12a,b, such that the portions 61,62 are assembled and the sensors 12a,b are received in the cutouts 66 (see FIGS. 5,6). It is important to note that the sensors 12a,b themselves extend from the skin contact surface 111 by a distance X, thus providing for improved contact with the skin of the wearer. In particular, the sensors 12a,b can have a conductive portion 72 of the surface 68 (i.e. coupled to the communication pathways 30 extending through backing material 74) as well as the raised backing material 74 to provide for the respective extension of the conductive portion 72 of the sensors 12a,b from the surface 111. For example, the backing material 74 can be comprised of electrically insulative interlaced fibres interleaved with the textile fibres incorporating the material (i.e. electrically insulative fibres) of the band portion 62.

Figure 8:
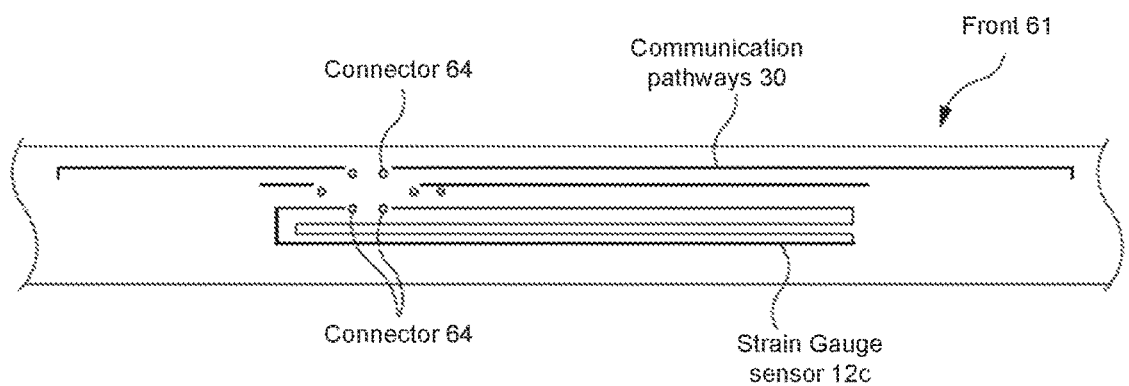
Figure 9:
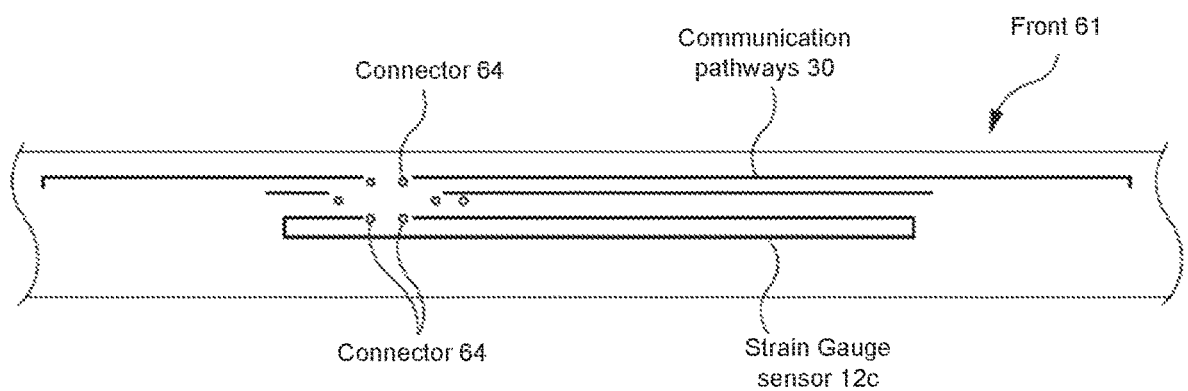

Referring to FIG. 8, shown is a further embodiment of the band portion 61 showing the strain gauge sensor 12c woven/knit in a serpentine fashion with other insulative fibres comprising the material of the band portion 61. As such, as shown in FIG. 7, it is recognized that once assembled, the band portion 62 would cover the strain gauge sensor 12c and thus insulate the skin of the wearer from direct contact with the electrically conductive fibres of the strain sensor 12c. FIG. 9 shows a further geometrical configuration of the strain sensor 12c.

Referring to FIGS. 5 to 8, it is recognized that they contain example geometrical layouts of the communication pathways 30 (e.g. traces) and the strain sensor 12c itself. The shown construction of the sensors 12a,b,c and band portions 61,62 are advantageous, as the entire pattern (of pathways 30 and sensor(s) 12c) is actually contained within covering portions 60,62 as one assembled (e.g. interlaced) layer of fabric, however the traces (of pathways 30 and sensor(s) 12c) are knitting inside the knit pattern and therefore as a consequence of that are insulated, therefore inhibiting any necessity of external insulation (glues, laminates, etc). in order to inhibit undesirably application of electrical charge from the traces to the skin of the wearer. Further, the 3D shape (e.g. extension from the surface 111) of the sensors 12a,b themselves can improves the sensors 12a,b contact with the skin and can provide for the collection of biometric data across a variety of skin conditions, dry or wet.

Interaction of Wearer 8 with Networked Devices 60

Figure 10:
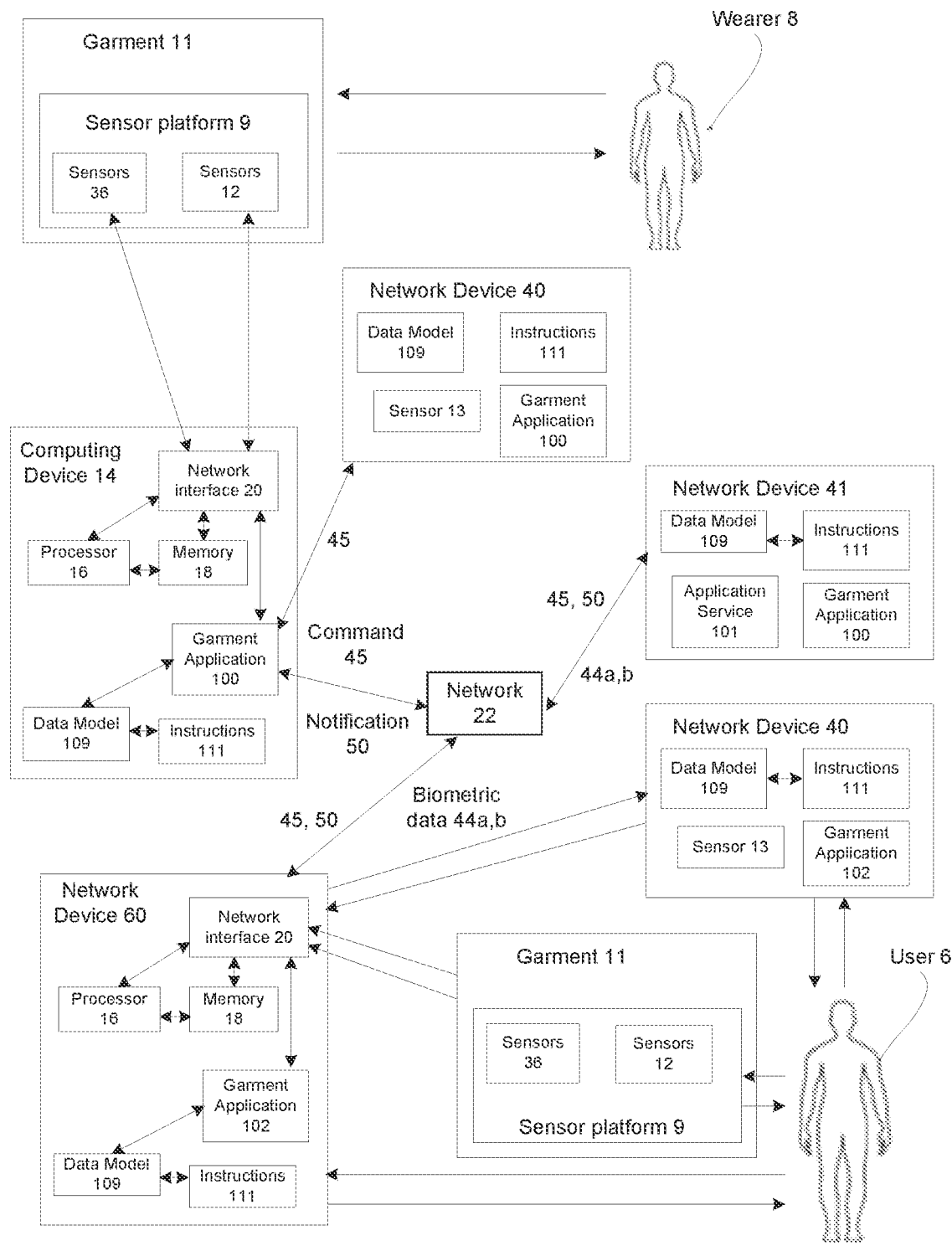
FIG. 10 shows a block diagram of a system for processing biometric data and acting thereon for the sensor platform shown in FIG. 1a, by example.

Referring to FIG. 10, shown is a garment application 100 bi-directionally communicating over the network 22 with a plurality of networked devices 60, each having a device application 102 capable of sending and receiving data 44a,b,45 (i.e. bidirectional) with the garment application 100 via the network 22. It is recognized that the garment application 100 can receive biometric data 44a,b via the interface 20 (e.g. API) and then can send the commands 45 based on the data 44a,b (e.g. raw or otherwise processed) to: the sensor platform 9 (from which the biometric data 44a was collected); and/or to one or more networked devices 60 in order to influence the operation of the networked device 60 (e.g. of their corresponding sensor platform 9, of the predefined device functionality such as music selection/playing, etc.) via the device application 102 running on the device 60. For example, the device application 102 can be a thermostat application 102 running on a home thermostat 60 and thus able to instruct the thermostat 60 to raise or lower the temperature setting controlled by the thermostat, recognizing that there are further bidirectional use cases described by example below. Further, as described above, the device 60 can have its own sensor platform 9 and thus capable of collecting and/or expressing sensory input/output via the sensors 12. It is recognized that both the wearer 8 and the user 6 can have devices 14, 60, 40 that have sensor platforms 9 and/or predefined device functionality (e.g. temperature modulation, music playing, etc.). It is recognized that the sensors 12 can be used to generate a number of sets (e.g. first set, second set, etc.) of the biometric data in order for the network device to monitor the effectiveness/effect of changing the operational characteristic. For example, when the temperature setting of the networked device 60 is changed to increase/decrease the temperature (based on a first set of the biometric data), a second set of the biometric data from the sensors 12 should indicated that the skin temperature of the wearer has increased/decreased.

The garment application 100 can receive the biometric data 44a,b collected by the sensors 12,36 incorporated in the garment 11 (e.g. shirt, pants/shorts, vest, underclothing, hat, and/or any other garment type incorporating the sensors 12,36 as part of or external to the band 10). The garment application 100 can interact with other external computer networked devices 60 (see FIG. 10 such as but not limited to music systems devices 60, heating system devices 60, lighting system devices 60, and other devices 60 having sensor platforms 9 configured to interact with the wearer 8 of the garment 11 via the garment application 100). It is recognized that the garment application 100 can be one or more applications 100 running on one or more computer platforms, for example such as but not limited to the garment application 100 executing on the computer device 14, the garment application 100 executing on the external device 40 (e.g. wearer's mobile device), and/or a cloud-based garment application 100 hosted on a wearer account on a network server 41, as desired. In any event, regardless of the one or many differently hosted garment applications 100, the garment application(s) 100 is/are configured to receive the biometric data 44a,b collected from the sensors 12,36 by the computer processor 16, optionally process or otherwise analyze the biometric data 44a,b, compare the data 44a (i.e. raw or processed) against one or more stored thresholds or rule sets 45 (further described below), to generate a command 45 for instructing the device application 102 to modify functional behavior(s) (e.g. operational characteristic) of the respective networked device 60, to communicate with the networked device 60 the command 45 as well as provided responses 45 (e.g. an acknowledgement that the networked device 60 received the data, processed the data, etc.) to the command from the networked device 60 in response to receiving the command 45. As further described below, the command 45 can be generated by the garment application 100 in response to a determined mood and/or temperature of the wearer based on a combination of sensed data 44a,b (e.g. activity, heartrate, etc.).

Similarly, the garment application 102 can receive the biometric data 44a collected by the sensors 12,36 incorporated in the garment 11 (e.g. shirt, pants/shorts, vest, underclothing, hat, and/or any other garment type incorporating the sensors 12,36 as part of or external to the band 10). The garment application 102 can interact with other external computer networked devices 14 (see FIG. 10 such as but not limited to music systems devices 14, heating system devices 14, lighting system devices 14, and other devices 14 having sensor platforms 9 configured to interact with the user 6 of the garment 11 via the garment application 102). It is recognized that the garment application 102 can be one or more applications 102 running on one or more computer platforms, for example such as but not limited to the garment application 102 executing on the computer device 60, the garment application 102 executing on the external device 40 (e.g. user's mobile device), and/or a cloud-based garment application 102 hosted on a user account on a network server 41, as desired. In any event, regardless of the one or many differently hosted garment applications 102, the garment application(s) 102 is/are configured to receive/generate the biometric data 44a,b collected from the sensors 12,36 by the computer processor 16, optionally process or otherwise analyze the biometric data 44a, compare the data 44a (i.e. raw or processed) against one or more stored thresholds or rule sets (further described below), to generate a command 45 for instructing the device application 100 to modify functional behavior(s) of the respective networked device 14, to communicate with the networked device 14 the command 45 as well as provided responses 45 to the command from the networked device 14 in response to receiving the command 45. As further described below, the command 45 can be generated by the garment application 102 in response to a determined mood and/or temperature of the user 6 based on a combination of sensed data 44a (e.g. activity, heartrate, etc.).

Figure 11:
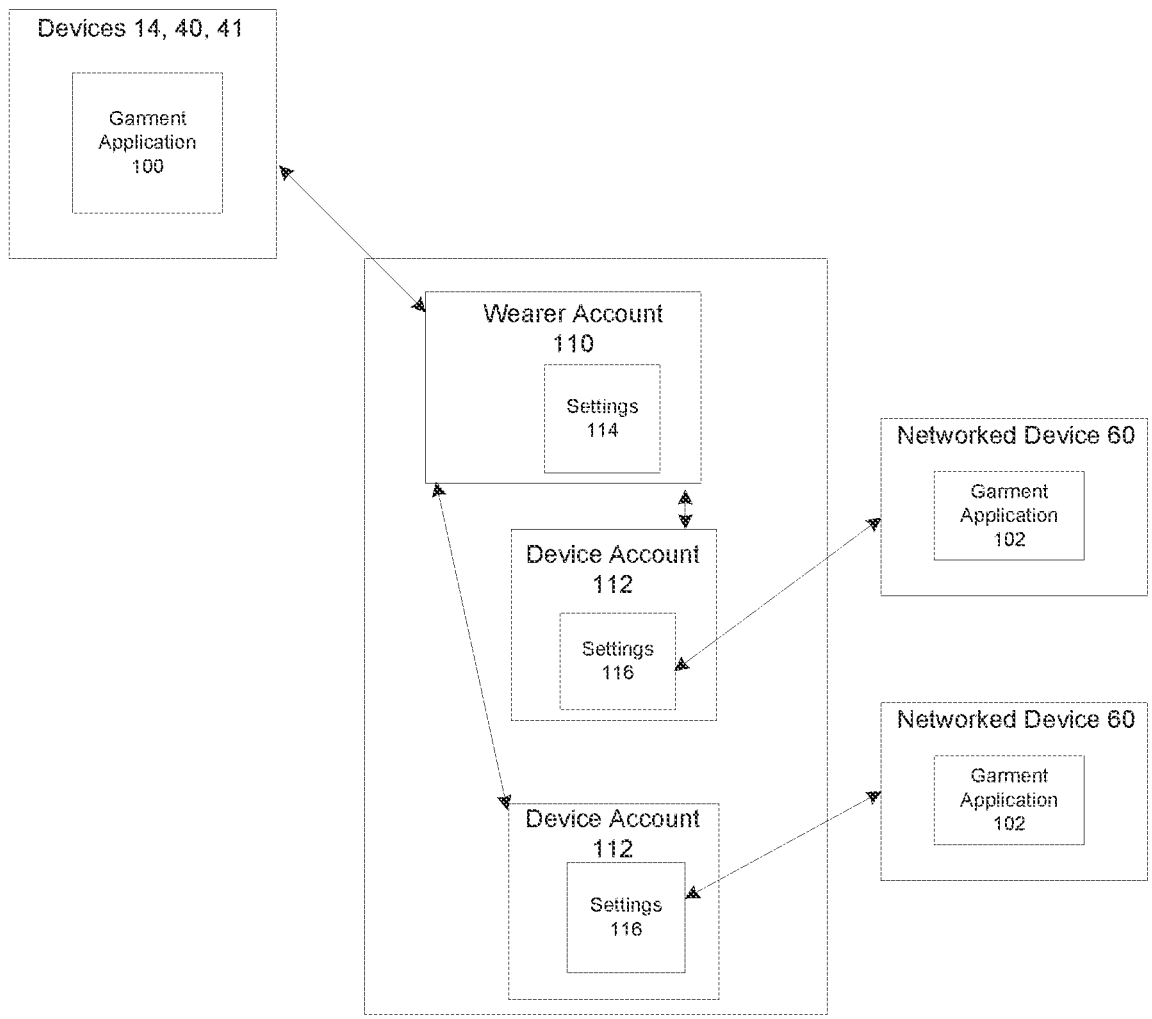
FIG. 11 is a block diagram of an interaction service for the system of FIG. 10.

Referring again to FIG. 10, a garment interaction service 101 can be implemented on the server 41, for example, however it can also be in whole or in part hosted on the external device 40, as desired. The garment interaction service 101 (see FIG. 11) contains a wearer account 110 registered with the garment application 100, as well as respective device accounts 112 (i.e. user 6 account) registered with their respective device application 102 of their networked device 60. The accounts 110,112 are registered with the service 101 prior to network 22 interaction therebetween. For example, a wearer 8 of device 14 wishing to communicate with devices 60 of the user 6, and vice versa, can register with the interaction service 101 as well as register the network device applications 100,102, thus creating accounts 110,112. Using the accounts 110,112, the interaction service 101 can receive data 44a,b, commands 45, and responses 45, thereby acting as a third party server/service for use in coordinating the network 22 interaction between the wearer 8 and the user 6.

The accounts 110,112 can contain registration information such as but not limited to: wearer/user login and password account information, wearer/user settings information 114 for device 14,60 operation (e.g. desired device 14,60 operation based on wearer/user parameter settings), device operation settings 116 (e.g. permitted functionality accessible to modify based on received commands 45), etc. It is recognized that the sensors 12 can be used to generate a number of sets (e.g. first set, second set, etc.) of the biometric data in order for the network device to monitor the effectiveness/effect of changing the operational characteristic. For example, when the operational characteristic setting of the networked device 60 is changed (based on a first set of the biometric data), a second set of the biometric data from the sensors 12 should indicate that measured biometric data of the wearer has increased/decreased accordingly (i.e. the networked device 60 can be used to analyze the biometric data from the sensors over time—by comparing the first set against the second set and subsequent sets) to see if the changes to the operational characteristic are having an effect on the wearer (causing the magnitude to change of the sensed parameter represented by the biometric data—e.g. temperature, activity level, attitude of the wearer's body, etc.), as expressed by the continually/periodically sampled biometric data via the sensors 12.

For example, in terms of wearer/user settings information 114, the wearer/user can specify music type selections (as played by music system device 60) for different wearer/user moods such as but not limited to "easy listening" music for active but considered happy/content wearer mood, "restful listening" music for use in calming the wearer during restful situations (e.g. sleep), "active listening" music for use in motivating the wearer to become more physically active, etc. Other settings 114 can include such as but not limited to: desired lighting levels (as moderated by lighting system device 14,60) based on determined wearer activity level/mental state, desired temperature settings (as moderated by heating/cooling system device 14,60) based on determined wearer activity level/mental state, operational mode of automobile (as moderated by automotive system device 14,60) based on determined wearer activity level/mental state, and/or the garment 11 itself based on functional devices of the sensor platform 9 resident on/in the garment 11 fabric such as but not limited to actuators (e.g. electronic sensors 12 capable of applying an electrical/vibrational stimulus to the wearer/user, heating device 12 capable of applying heat to the wearer/user, cooling device 12 capable of removing heat or otherwise cooling the wearer/user, and/or any other device 12 that can change its functional state based on receiving of the command 45 generated using sensed and processed (e.g. via application 100) biometric data 44a,b. Another example of wearer/user settings information 114 is for location settings, such that the wearer/user can specify the definition of certain physical locations (e.g. geolocation X represents the wearer's home, geolocation Y represents the wearer/user work/employment, geolocation Z represents the wearer/user preferred hobby, geolocation X1 represents the wearer/user location within the home—e.g. bedroom, etc.). It is also recognized that the wearer/user settings information 114 can be used to define the wearer/user environment based on co-registration of the device 14,60 with an adjacent device (e.g. pairing the device with the external device 40 can be used to indicate when the wearer/user is exercising at their gym, driving their car, etc.). As such, it is recognized that the garment application 100,102 can also be informed of the wearer/user activity/mental state based on information obtained from sensors/devices 12,13 (e.g. current Bluetooth connectivity with another device 14,60 such as an automotive communication system, GPS sensors resident on the external device 40, etc.).

In view of the above, it is recognized that the garment application 100,102 is responsible for receiving the biometric data 44a,b on a periodic (e.g. determined regular frequency of data 44a,b reporting) basis and/or on a requested basis (e.g. in response to a command 45 generated, and sent to the networked device 14,60 which in turn changes an operational state of the networked device 14,60). In this way, scheduled periodic and/or upon request, the garment application 100,102 can be used to monitor the physical/mental state of the wearer/user over a period of time, and as instructed by the wearer/user settings 114, can adjust the operational functionality of one or more of the networked devices 14,60 based on received and interpreted biometric data 44a,b.

It is recognized that the garment application 100,102 can have access to a plurality of data models 109 for use in comparing a plurality of biometric data 44a,b from two or more different sensor types (e.g. activity sensor and temperature sensor, temperature sensor and ECG sensor, activity sensor and posture sensor, activity sensor and location sensor, etc.). The data models 109 each represent a series of data 44a,b value combinations, which define a particular desired (or undesired) physical/mental state of the wearer/user (for example as defined by the wearer/user). For example, data 44a,b can comprise; 1) a location of the home (e.g. bedroom), a time of day (e.g. nighttime), a temperature reading (e.g. elevated), and an activity reading (e.g. wearer/user motion), 2) can be received by the garment application 11 and 3) compared to a data model 109 representing a desired sleep pattern for the wearer/user. In the event that the data 44a,b matches the desired sleep pattern of the sleep data model 109, the garment application 100,102 would not generate any commands 45 and thereby attempt to moderate or otherwise affect any networked devices 14,60 (e.g. thermostat 60, music system 60, etc.) associated with the sleep data model 109.

Figure 12:
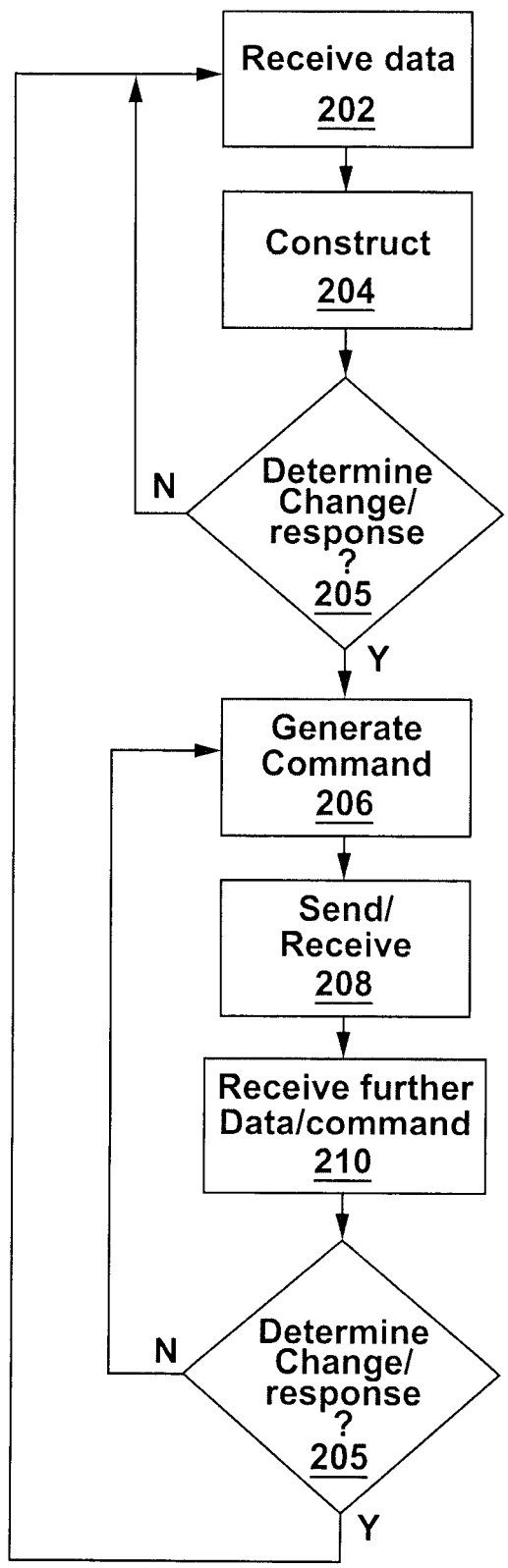
FIG. 12 is a flowchart of an example operation of the system of FIG. 10.

As such, referring to FIG. 12 for command operation 200, the garment application 100 receives 202 the biometric data 44a,b (as well as any other data provided by third party devices such as but not limited to the external device 40), comprising multiple data types collected/received from the sensors 12,36. For example, the garment application 100 can be configured to receive periodically (e.g. every 10 seconds) data 44a,b from each of the sensors 12,36 of the garment 11. In response to the received 202 data 44a,b, the garment application 100 can construct 204 the data 44a,b for the command/notification 45 based on the collected data 44a,b and generate 206 one or more command/notifications 45. It is recognized that each of the data models 109 would have a set of instructions 111 (see FIG. 10) for use in determining/suggesting what action(s) is/are appropriate in the event that the data 44a,b matches (or does not match), and to what degree, the data patterns implicit in the data model(s) 109 match or do not match the plurality of data 44a,b (of different data types) provided by the sensors 12,36.

Sleep Example

One example of operation, following FIG. 12, of the garment application 100 is for monitoring 200 a sleep or restful state of the wearer 8. For example, the garment 11 by way of the sensor 12,36 data received 202 by the garment application 100 can indicate an activity level (e.g. accelerometer data 44a,b) of the wearer 8, a temperature level (e.g. temperature sensor data 44a,b) of the wearer 8, and a posture or body attitude level (e.g. strain sensor or gyroscopic data 44a,b) of the wearer 8. The garment application 100 can compare 204 these received data 44a,b levels to one or more sleep patterns/thresholds of the sleep data model 109 in order to determine 205 if the wearer 8 is having a sleep episode that matches (e.g. representing a restful sleep) or does not match (e.g. represents a disturbed/fit full sleep) the sleep pattern(s) of the sleep data model 109. At step 206, based on the degree of match or mismatch, the garment application 100 can generate 206 a command 45 for a) one or more of the networked devices 60 and/or b) for one or more sensors/actuators 12 of the sensor platform 9 (as associated with the data mode 109 via the instructions 111) and send 208 the command(s) to the sensor platform 9 (via the computing device 14) and/or to the networked device 60 and receive feedback 45 (e.g. an acknowledgement response, a response indicating a change or degree of change in operational function of the networked device 60, further biometric data 44a from the sensor platform 9 resultant form processing of the command 45) from the sensor platform 9 and/or the networked device 60.

In the case of the sleep example, the garment application 100 of the network device 40 can generate 206 an increase temperature command 45 by a defined amount (e.g. by 2 degrees Centigrade), based on the set of rules 111, and send 208 the command 45 to the thermostat 60 and/or to the sensor platform 9 of the wearer 8. The garment application 100 can receive acknowledgement 45 of the temperature increase command from the thermostat 60 and/or the sensor platform 9 (via the computing device 14) and can subsequently monitor 210 (e.g. via further programmed periodic or requested data) further data 44a of the wearer 8 to determine via a further data model 109 comparison 212 whether the new/revised data 44a (a consequence of the issued command 45) represents a desired change (e.g. improvement) 213 in the wearer's activity/mental state represented by the data model 109, or lack of improvement thereof. In the case of a desired change at step 213, the garment application 100 would refrain from issuing further commands 45 to the networked device 60 (and/or to the sensor platform 9) and thus continue to monitor 202 the wearer 8 via further periodic receipt of the data 44a and comparison to the data model(s) 109. If the change/no change determined at step 213 needs further commands 45 to be issued (e.g. sleep has improved but not to an acceptable level as represented in the model 109 data patterns), the garment application 100 returns to step 206.

In the above example, one potential data pattern of the sleep data model 109 is where the wearer's 8 temperature is low (e.g. wearer is too cold) and the wearer's activity/motion level is also elevated (e.g. wearer is tossing and turning). The command 45 issued would be to increase the room temperature to the thermostat 60 and/or to the sensor platform 9 (to use the heat actuators 12 to increase the temperature of the heat actuators 12 in the sensor platform 9) and the garment application 100 would monitor the effect of the temperature change, e.g. an increasing of the wearer temperature. Subsequent monitored increasing of the wearer 8 activity level via the new data 44a to acceptable levels as defined in the sleep data model 109 would return the garment application 100 to operating at step 202. On the contrary, subsequent monitored lowering/unchanged of the wearer 8 activity level via the new data 44a representing non-acceptable levels as defined in the sleep data model 109 would return the garment application 100,102 to operating at step 206, in an effort to continued increasing of the room temperature (or the garment 11 temperature via the heat actuators 12) in order to facilitate an increase in the wearer's 8 body temperature and/or decrease in activity level. It is also recognized that the method 200 can be used to activate (by the user 6) one or more of the sensors 12 of the sensor platform 9 of the wearer 8, in order to provide a sensory output to the wearer 8, e.g. a pat/rub on the back, etc. As such, it is recognized that the social example of reassuring or otherwise interacting with someone remotely (i.e. the user 6 with the wearer 8) in response to a sensed activity (e.g. sleep) or other mental/physical state of the wearer 8 as reported 45 by their sensor platform 9 to the device 60 of the user 6, is provided for.

In view of the above sleep example, it is recognized that the collected biometric data 44a can be periodically monitored by the application 100 of the network device 40 of the wearer 8, as the biometric data 44a is interpreted by the application 100 and commands 45 are generated to effect further operation of actuators 12 in the sensor platform 9 of the wearer 8. In view of the above sleep example, it is recognized that the collected biometric data 44a can be periodically monitored by the application 100 of the network device 40 of the wearer 8, as the biometric data 44a is interpreted by the application 100 and commands 45 are generated to effect further operation other networked devices 60 in the vicinity of the wearer 8. In view of the above sleep example, it is recognized that the collected biometric data 44a can be periodically monitored by the application 100 of the network device 40 of the wearer 8, as the biometric data 44a is interpreted by the application 100 and commands 45 are generated to effect further operation other networked devices 60 in the vicinity of the wearer 8 as well as the sensors/actuators 12 to effect further operation of actuators 12 in the sensor platform 9 of the wearer 8.

Medical Example

It is recognized that the number of potential applications for the garment 11 paired with the garment application 100 and the device application(s) 102 can be numerous. A further example is where the garment application 100 detects (i.e. via the sensed data 44a) an elevated heart rate (still with acceptable norms—i.e. not indicative of a heart attack) without a corresponding increase in physical activity level. This physical state of the wearer 8, as defined/matching a data model 109, could be indicative of an anxiety or heart attack or other physical symptom of a medical disease/condition being treated by the user 6 (i.e. the medical practitioner with the wearer 8 as their patient). In this case, the garment application 100 could be programmed via the instructions 111 of the data model 109 to instruct/report to a networked device 60 of the user 6 the periodic/real-time physical state of the wearer 8.

It is recognized that the data model 109 by way of the instructions and data patterns 111 can be used to define more complex state(s) of the wearer 8, via a combination of a plurality of the various sensor 12,36 types and their data. For example, the current mental state (e.g. happy, sad, anxious, excited, sedate, depressed, relaxed, etc.) can be determined as a result of a combination of the plurality of sensed data 44a,b matching (or not matching) the data model(s) 109 representing that mental state. For example, the data 44a,b for heart rate, temperature, activity level, and posture can be used, as a combination, to define and predict the current mental/physical state of the wearer 8, based on the mental/physical state modelling as represented by a mental/physical state data model 109.

Further Medical Example

A further example is where the garment application 100 detects (i.e. via the sensed data 44a) an elevated swelling in a limb of the wearer 8. This physical state of the wearer 8, as defined/matching a data model 109, could be indicative of a physical symptom of a medical disease/condition being treated by the user 6 (i.e. the medical practitioner with the wearer 8 as their patient). In this case, the garment application 100 could be programmed via the instructions 111 of the data model 109 to generate commands 45 (i.e. the biometric data 44b) to actuate the actuators 12 in the sensor platform 9 to apply pressure to the areas of swelling, in an attempt to affect the periodic/real-time physical state of the wearer 8.

It is recognized that the data model 109 by way of the instructions and data patterns 111 can be used to define more complex state(s) of the wearer 8, via a combination of a plurality of the various sensor 12,36 types and their data. For example, the current physiological state can be determined as a result of a combination of the plurality of sensed data 44*a* matching (or not matching) the data model(s) 109 representing a desired physiological state. For example, the data 44*a* for swelling, temperature, and posture can be used, as a combination, to define and predict the current physiological state of the wearer 8, based on the physiological state modelling as represented by a physiological state data model 109.

Notification Emergency Example

It is also recognized that in the event that the operation 200, as shown in FIG. 12, does not mitigate or otherwise obviate the determined match/mismatch of the data model(s) 109 performed by the garment application 100 using the sensed data 44*a* (i.e. as determined via the comparisons with the data model 109), the garment application 100 could be programmed via the settings 114 to send a notification 50 to a specified device 60 indicating a potential emergency/crisis event. For example, this specified device 60 could be that of a family member, medical practitioner, notification service, or friend, which would receive the notification 45 and could be informed of the wearer's activity/mental state and/or otherwise encouraged to perform some action (e.g. contact the wearer 8, contact a medical practitioner, etc.)—see FIG. 10. The device 60 could also be the external device 40 of the wearer 8, thus providing the wearer 8 with direct indication of their situation (e.g. "you are too excited and maybe you need to calm down?").

It is also recognized that the operation 200 could be used to determine an actual considered detrimental/emergency condition of the wearer 8, e.g. heart attack, car accident or other body trauma, kidnapping, etc., such that the data models 109 are used to indicate/determine (by the garment application 100 comparing the data 44*a* to the rules and data patterns 111 of the data model 109) that the data 44*a* is well outside (or inside) expected norms/thresholds defined in the data models 109. For example, the data 44*a* when compared to the data models 109 could indicate a heart attack (e.g. via ECG readings 44*a* and activity readings 44*a*), a stroke (e.g. EGC readings 44*a* and activity level readings 44*a*), kidnapping (e.g. anxiety level readings 44*a*, activity level readings 44*a* and location/change in location readings 44*a*), etc.

Mental/Physical Activity Example

A further example operation 200 can be for a planned physical activity (e.g. cycling, jogging) of the individual wearer 8. The data model 109 representing the mental activity/state can be used by the garment application 100 to monitor the wearer's biometric data 44*a*, and to report to the user 6 via the computer device 60 (e.g. sound, light or other haptic commands/sensations 44*b*) and/or via the external device 40 (e.g. sound and/or messages on a screen of the device 40) and therefore based on that the user 6 could send suggestions 45 to the wear 8 while performing the activity. For example, focus levels (e.g. mental state) of the wearer 8 can be monitored by the garment application 100, via the sensed data 44*a* and comparison to the data model(s) 109 representing the activity (for example as a result of monitored body posture, breathing rate, heart rate, etc.), and thus a notification (e.g. command 45) can be sent to the wearer 8 (i.e. via the device 14,40) by the user 6 indicating that focus levels are outside of a threshold (e.g. too low) and thus the wearer 8 should correct (e.g. refocus). Again, as per the operation 200 described above, the dynamic mental state of the wearer 8 could be continually monitored by the garment application 100, and therefore informed to the user 6 (in comparison of data 44*a,b* with the data model 109) and thus further suggestions (e.g. of refocus) 45 would be sent to the wearer 8. Alternatively, a notification 45 of the detected mental state (e.g. focus) back within accepted norms could be sent to the wearer 8 as a consequence of the continued monitoring.

It is also recognized that the data model(s) 109 could be used to detect the type of physical activity being performed by the user/wearer (e.g. yoga, cycling, etc.), based on the sensed data 44*a,b* matching a particular activity type pattern. Once detected, the garment application 100 could select an use an appropriate data model 109 representative of the detected activity type to inform the user 6 of the state (e.g. physical/mental) of the wearer 8 as the activity is being performed. The physical activity can be an activity such as but not limited to; vigorous physical activity such as a physical sport (e.g. cycling, running, weight training, etc.) non-vigourous physical activity/sport (e.g. dart throwing, yoga, tai chi, etc.); active/concentrated mental activity such as computer work at the wearer's place of employment; relaxed mental activity such as reading/relaxation/listening to music/meditation; etc. In any event, it is recognized that the data models 109 can be used to optionally detect and to also monitor the physical/mental activity of the wearer 8, based on the sensed data 44*a,b* in comparison to the requisite data model(s) 109 as discussed above with respect to the operation 200.

Data Processing System 300

Referring to FIG. 13, shown is a block diagram of the data processing system 300. It is recognized that the data processing system 300 can be implemented on any one or more of the devices 40,41,60 as desired. Each device 40,41,60 typically comprises a land-based network-enabled personal computer. However, the invention is not limited for use with personal computers. For instance, one or more of the network devices 40,41,60 can comprise a wireless communications device, such as a wireless-enabled personal data assistant, a tablet, or e-mail-enabled mobile telephone if the network 22 is configured to facilitate wireless data communication. The device 40,41,60 is capable of supplying the data 44*a,b* to the system in order to determine/generate the model(s) 109 as well as to utilize the stored model(s) 109 predict/report real time mental/physiological state as described by example. The user (e.g. wearer 8, user 6, system administrator, analyst, etc.) of the device 40,41,60 can interact with the data 44*a,b* as provided.

As shown in FIG. 13, the data processing system 300 can comprise a network interface 302 coupled to the network 22, the user interface 304 for receipt and presentation (e.g. via text, sound, pictures, video, light and/or haptic feedback) of data 44*a,b*, commands 45, and the data collection/processing sensor platform 9 in communication with the network interface 302 and the user interface 304 (e.g. via the computing device 14). Typically, the network interface 302 comprises an Ethernet network circuit card, however the network interface 302 may also comprise an RF antenna for wireless communication over the communications network 22. Preferably, the user interface 304 comprises a data entry device (such as keyboard, microphone or writing tablet), and a display device (such as a CRT or LCD display). The data processing system 300 includes a central processing unit (CPU) 308, and a non-volatile memory storage device (DISC) 310 (such as a magnetic disc memory or electronic memory) and a read/write memory (RAM) 312 both in communication with the CPU 308. The DISC 310 includes data which, when loaded into the RAM 312, comprise processor instructions for the CPU 308 which define memory objects for allowing the device 40,41,60 to operate the applications(s) 100,102.

Storage 310 Examples

In view of the above descriptions of storage 310, the storage 310 can be configured as keeping the stored data (e.g. models 109 and related data) in order and the principal (or only) operations on the stored data are the addition of and removal of the stored data from the storage (e.g. FIFO, FIAO, etc.). For example, the storage 310 can be a linear data structure for containing and subsequent accessing of the stored data and/or can be a non-linear data structure for containing and subsequent accessing of the stored data (e.g. models 109, associated model data such as features, effects, etc., data 44a,b, applications 100,102, etc.). Further, the storage 310 receives various entities such as applicable data/instructions that are stored and held to be processed later. In these contexts, the storage 310 can perform the function of a buffer, which is a region of memory used to temporarily hold data while it is being moved from one place to another. Typically, the data is stored in the memory when moving the data between processes within/between one or more computers. It is recognized that the storage 310 can be implemented in hardware, software, or a combination thereof. The storage 310 is used in the system when there is a difference between the rate/time at which data is received and the rate/time at which the data can be processed.

Further, it will be understood by a person skilled in the art that the memory/storage 310 described herein is the place where data can be held in an electromagnetic or optical form for access by the computer processors/modules 40,41,60. There can be general usages: first, memory is frequently used to mean the devices and data connected to the computer through input/output operations such as hard disk and tape systems and other forms of storage not including computer memory and other in-computer storage. Second, in a more formal usage, memory/storage has been divided into: (1) primary storage, which holds data in memory (sometimes called random access memory or RAM) and other "built-in" devices such as the processor's L1 cache, and (2) secondary storage, which holds data on hard disks, tapes, and other devices using input/output operations. Primary storage can be faster to access than secondary storage because of the proximity of the storage to the processor or because of the nature of the storage devices. On the other hand, secondary storage can hold much more data than primary storage. In addition to RAM, primary storage includes read-only memory (ROM) and L1 and L2 cache memory. In addition to hard disks, secondary storage includes a range of device types and technologies, including diskettes, Zip drives, redundant array of independent disks (RAID) systems, and holographic storage. Devices that hold storage are collectively known as storage media.

A database is one embodiment of memory 310 as a collection of information that is organized so that it can easily be accessed, managed, and updated. In one view, databases can be classified according to types of content: bibliographic, full-text, numeric, and images. In computing, databases are sometimes classified according to their organizational approach. The most prevalent approach is the relational database, a tabular database in which data is defined so that it can be reorganized and accessed in a number of different ways. A distributed database is one that can be dispersed or replicated among different points in a network. An object-oriented programming database is one that is congruent with the data defined in object classes and subclasses. Computer databases typically contain aggregations of data records or files. Typically, a database manager provides users the capabilities of controlling read/write access, specifying report generation, and analyzing usage. Databases and database managers are prevalent in large mainframe systems, but are also present in smaller distributed workstation and mid-range systems such as the AS/400 and on personal computers. SQL (Structured Query Language) is a standard language for making interactive queries from and updating a database such as IBM's DB2, Microsoft's Access, and database products from Oracle, Sybase, and Computer Associates.

Memory/storage can also be defined as an electronic holding place for instructions and data that the computer's microprocessor can reach quickly. When the computer is in normal operation, its memory usually contains the main parts of the operating system and some or all of the application programs and related data that are being used. Memory is often used as a shorter synonym for random access memory (RAM). This kind of memory is located on one or more microchips that are physically close to the microprocessor in the computer.

In terms of a server, it is recognized that the device 40,41,60 as host for the application(s) 100,102 can be configured as hardware, software, or typically a combination of both hardware and software to provide a network entity that operates as a socket listener via the network 22. It is recognized that any computerized process that shares a resource (e.g. data) to one or more client processes can be classified as a server in the network system. The term server can also be generalized to describe a host that is deployed to execute one or more such programs, such that the host can be one or more configured computers that link other computers or electronic devices together via the network 22. The server(s) can provide specialized services across the network 22, for example to private users inside a large organization or to public users via the Internet 22. In the network system, the servers can have dedicated functionality and/or can share functionality as described. Enterprise servers are servers that are used in a business context and can be run on/by any capable computer hardware. In the hardware sense, the word server typically designates computer models intended for running software applications under the heavy demand of a network 22 environment. In this client-server configuration one or more machines, either a computer or a computer appliance, share information with each other with one acting as a host for the other. While nearly any personal computer is capable of acting as a network server, a dedicated server will contain features making it more suitable for production environments. These features may include a faster CPU, increased high-performance RAM, and typically more than one large hard drive. More obvious distinctions include marked redundancy in power supplies, network connections, and even the servers themselves.

I claim:

1. A method of using a sensor platform bidirectionally, the sensor platform incorporated into a garment of a wearer using sensed biometric data, the method comprising:
   receiving, from sensors of the sensor platform, a set of biometric data;
   sending the set of biometric data to a garment application executing on a network device associated with the sensor platform, said garment application determining an area of swelling and a posture of said wearer based on said set of biometric data, and determining a physiological state of said wearer based on said area of swelling and said posture;

receiving, from the network device, a command in response to said set of biometric data, wherein said command is generated by said garment application in response to said physiological state of said wearer and said command contains generated biometric data;

applying the command via one or more actuators of the sensor platform to effect a change in an operational characteristic of at least one of the sensors of the sensor platform based on said generated biometric data contained in the command, said change in said operational characteristic comprising applying a pressure to said area of swelling;

receiving, from the sensors of the sensor platform, a set of further biometric data;

sending the set of further biometric data to the garment application, said garment application making a second determination of at least said area of swelling of said wearer based on said set of further biometric data, and to make a second determination of said physiological state of said wearer based on said area of swelling and said posture;

determining, based on said second determined physiological state of said wearer, that said command did not mitigate said physiological state of said wearer; and sending a notification to said network device that said wearer is in a potential emergency/crisis event.

2. The method of claim 1, wherein the garment is configured for wearing next to the skin of the wearer.

3. The method of claim 1, wherein at least one of the sensors is comprised of electrically conductive threads interlaced with non-conductive threads in a body layer of the garment.

4. The method of claim 1, wherein at least one of the sensors of the sensor platform is capable of both generating the biometric data as well as changing said operational characteristic in response to receiving the received biometric data contained in the command.

5. The method of claim 1, wherein the command contains received biometric data to generate via the sensors at least one of pressure or heat to simulate sensor signals generated by another sensor platform coupled to the network device.

6. The method of claim 1, wherein the command is a notification expressed as biometric data.

7. The method of claim 3, wherein the electrically conductive threads are structured as shape shifting alloy yarns for changing a shape of the sensor based on the command.

8. The method of claim 3, wherein the electrically conductive threads are structured as thermal yarns for generating heat via the sensor based on the command.

9. The method of claim 3, wherein the electrically conductive threads are structured as electromagnetic yarns for generating vibration via the sensor based on the command.

10. The method of claim 3, wherein the electrically conductive threads are structured as electrical stimulator yarns for generating an electrical pulse via the sensor based on the command.

* * * * *